United States Patent
Mobley et al.

(10) Patent No.: US 12,419,620 B2
(45) Date of Patent: Sep. 23, 2025

(54) CORE-SEVERING CANNULA FOR BIOPSY DEVICES

(71) Applicant: Argon Medical Devices, Inc., Athens, TX (US)

(72) Inventors: Matthew Mobley, Athens, TX (US); Venkata Ramana Hogirala, Athens, TX (US); Joe Cotten, Athens, TX (US)

(73) Assignee: Argon Medical Devices, Inc., Athens, TX (US)

( * ) Notice: Subject to any disclaimer, the term of this patent is extended or adjusted under 35 U.S.C. 154(b) by 94 days.

(21) Appl. No.: 16/989,665

(22) Filed: Aug. 10, 2020

(65) Prior Publication Data

US 2021/0052259 A1    Feb. 25, 2021

Related U.S. Application Data

(60) Provisional application No. 62/890,512, filed on Aug. 22, 2019.

(51) Int. Cl.
*A61B 10/02* (2006.01)
*A61B 17/34* (2006.01)
*B29C 67/24* (2006.01)

(52) U.S. Cl.
CPC ...... *A61B 10/0275* (2013.01); *A61B 10/0266* (2013.01); *A61B 17/3421* (2013.01); *B29C 67/24* (2013.01); *A61B 2010/0208* (2013.01); *B29C 2791/009* (2013.01)

(58) Field of Classification Search
CPC . A61B 10/0275; A61B 10/06; A61B 10/0208; A61B 10/0266; A61B 17/3421; B29C 67/24; B29C 2791/009
See application file for complete search history.

(56) References Cited

U.S. PATENT DOCUMENTS

| | | | |
|---|---|---|---|
| 5,573,008 A | 11/1996 | Robinson |
| 5,655,542 A | 8/1997 | Weilandt |
| 5,776,075 A | 7/1998 | Palmer |
| 5,779,647 A | 7/1998 | Chau et al. |
| 5,842,999 A | 12/1998 | Pruitt et al. |

(Continued)

FOREIGN PATENT DOCUMENTS

| | | | | |
|---|---|---|---|---|
| EP | 1759638 B1 * | 4/2009 | ............ | A61B 10/02 |
| WO | 2004045417 | 6/2004 | | |

(Continued)

OTHER PUBLICATIONS

European Patent Office, European Search Report and Written Opinion, European Patent Application No. EP20192069, Jan. 19, 2021, Germany.

*Primary Examiner* — Jennifer Robertson
*Assistant Examiner* — Nidhi N Patel
(74) *Attorney, Agent, or Firm* — IpHorgan Ltd.

(57) ABSTRACT

A core-severing cannula for use with tissue biopsy devices, comprising a plurality of flexible fingers for severing a tissue core. The core-severing cannula is positioned coaxially outside of a core-cutting cannula, and is slidable relative to the core-cutting cannula. As the device is activated, the core cutting cannula and core-severing cannula advance together to cut a core of tissue. Subsequently, the core-severing cannula is advanced relative to the core cutting cannula, and the fingers of the core-severing cannula assume a closed position to sever the core from the target site.

15 Claims, 27 Drawing Sheets

(56) References Cited

U.S. PATENT DOCUMENTS

| | | |
|---|---|---|
| 5,916,175 A | 6/1999 | Bauer |
| 5,951,489 A | 9/1999 | Bauer |
| 5,976,164 A | 11/1999 | Bencini et al. |
| 5,993,399 A | 11/1999 | Pruitt et al. |
| 6,120,463 A | 9/2000 | Bauer |
| 6,126,617 A | 10/2000 | Weilandt et al. |
| 6,283,925 B1 | 9/2001 | Terwilliger |
| 6,322,523 B2 | 11/2001 | Weilandt |
| 6,358,217 B1 | 3/2002 | Bourassa |
| 6,626,850 B1 | 9/2003 | Chau et al. |
| 6,676,658 B2 | 1/2004 | Burbank et al. |
| 6,679,851 B2 | 1/2004 | Burbank et al. |
| 6,969,358 B2 | 11/2005 | Baltschun et al. |
| 7,022,085 B2 | 4/2006 | Cooke et al. |
| 7,156,815 B2 | 1/2007 | Leigh et al. |
| 7,329,227 B2 | 2/2008 | Schramm |
| 7,470,237 B2 | 12/2008 | Beckman et al. |
| 7,585,282 B2 | 9/2009 | Hancock |
| 7,625,347 B2 | 12/2009 | Burbank et al. |
| 8,016,856 B2 | 9/2011 | Lavelle et al. |
| 8,172,773 B2 | 5/2012 | Heske et al. |
| 8,192,369 B2 | 6/2012 | Bacon et al. |
| 8,197,419 B2 | 6/2012 | Field et al. |
| 8,262,586 B2 | 9/2012 | Anderson et al. |
| 8,277,394 B2 | 10/2012 | Hibner |
| 8,282,574 B2 | 10/2012 | Coonahan et al. |
| 8,343,070 B2 | 1/2013 | Krueger |
| 8,343,072 B2 | 1/2013 | Bacon et al. |
| 8,366,636 B2 | 2/2013 | Videbaek |
| 8,460,204 B2 | 6/2013 | Quick et al. |
| 8,475,393 B1 | 7/2013 | Hameed |
| 8,506,504 B2 | 8/2013 | Field et al. |
| 8,628,482 B2 | 1/2014 | Leimbach et al. |
| 8,636,734 B2 | 1/2014 | Burbank et al. |
| 8,690,793 B2 | 4/2014 | Ranpura et al. |
| 8,734,363 B2 | 5/2014 | Bacon |
| 8,771,199 B2 | 7/2014 | Theobald et al. |
| 8,771,200 B2 | 7/2014 | Thompson et al. |
| 8,814,856 B2 | 8/2014 | Elmouelhi et al. |
| 8,968,211 B2 | 3/2015 | Ferree et al. |
| 8,979,768 B2 | 3/2015 | Privitera et al. |
| 9,060,759 B2 | 6/2015 | Williams et al. |
| 9,072,508 B2 | 7/2015 | Callede et al. |
| 9,101,347 B2 | 8/2015 | Mcghie et al. |
| 9,113,856 B2 | 8/2015 | Callede et al. |
| 9,149,293 B2 | 10/2015 | Hardert et al. |
| 9,155,527 B2 | 10/2015 | Vetter et al. |
| 9,220,484 B2 | 12/2015 | Krueger |
| 9,282,948 B2 | 3/2016 | Melchiorri et al. |
| 9,332,973 B2 | 5/2016 | Mcweeney et al. |
| 9,392,998 B2 | 7/2016 | Snow |
| 2003/0163152 A1 | 8/2003 | Weilandt et al. |
| 2004/0068231 A1 | 4/2004 | Blondeau |
| 2004/0158172 A1 | 8/2004 | Hancock |
| 2008/0200834 A1* | 8/2008 | Mark ............... A61B 17/3403 600/566 |
| 2008/0281226 A1 | 11/2008 | Peters |
| 2011/0004120 A1 | 1/2011 | Drubetsky |
| 2012/0265097 A1 | 10/2012 | Melchiorri |
| 2013/0102925 A1* | 4/2013 | McGhie ............ A61B 10/0233 600/567 |
| 2013/0197393 A1 | 8/2013 | Ritchart |
| 2014/0207021 A1 | 7/2014 | Snow |
| 2014/0276208 A1 | 9/2014 | Mcghie |
| 2014/0371585 A1 | 12/2014 | Thompson et al. |
| 2015/0005663 A1 | 1/2015 | Callede et al. |
| 2015/0201917 A1 | 7/2015 | Snow |
| 2015/0238171 A1 | 8/2015 | Shabaz |
| 2015/0272556 A1 | 10/2015 | Lee |
| 2016/0030018 A1* | 2/2016 | McWeeney ........ A61B 10/0275 600/566 |
| 2016/0249893 A1 | 9/2016 | Arnholt et al. |
| 2016/0361088 A1* | 12/2016 | Maguire ............ A61B 17/3415 |
| 2018/0153525 A1 | 6/2018 | Choi |
| 2018/0228476 A1* | 8/2018 | Cannon ................ A61B 10/04 |

FOREIGN PATENT DOCUMENTS

| | | |
|---|---|---|
| WO | 2006005342 | 1/2006 |
| WO | 2008106583 | 9/2008 |
| WO | 2014081812 | 5/2014 |
| WO | 2014113665 | 7/2014 |

* cited by examiner

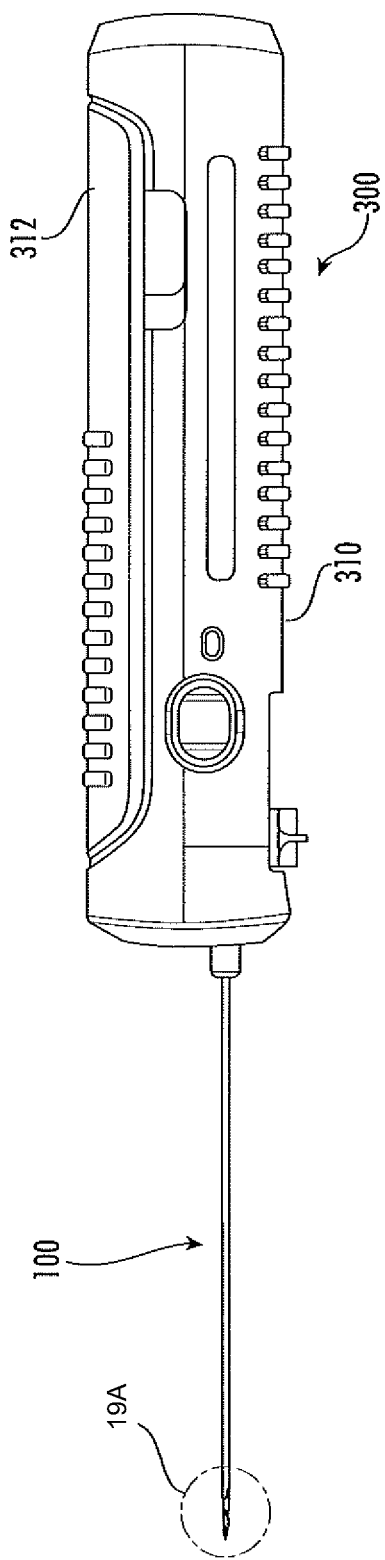
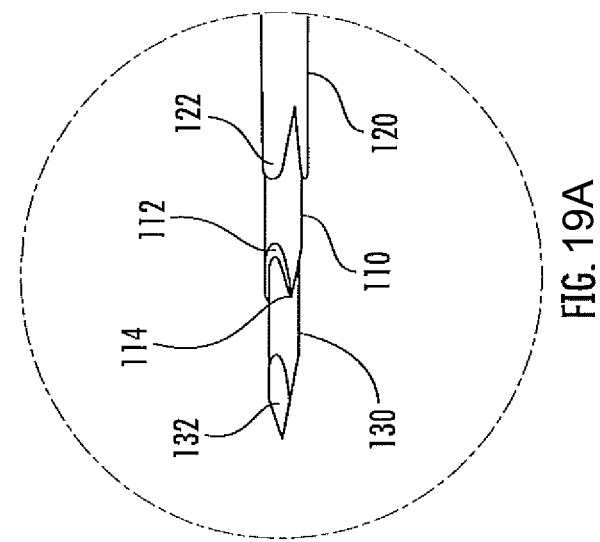
FIG. 19
FIG. 19A

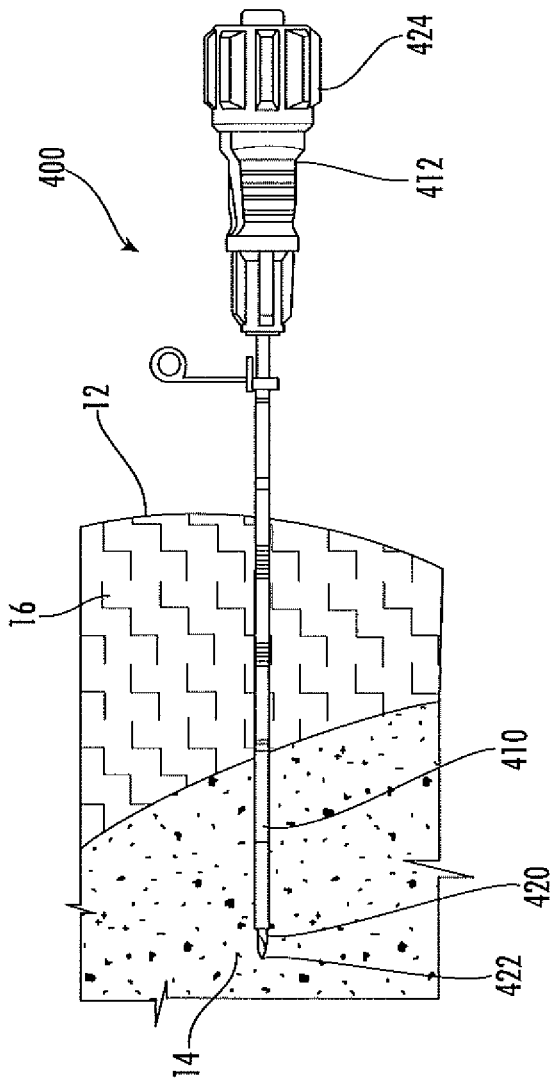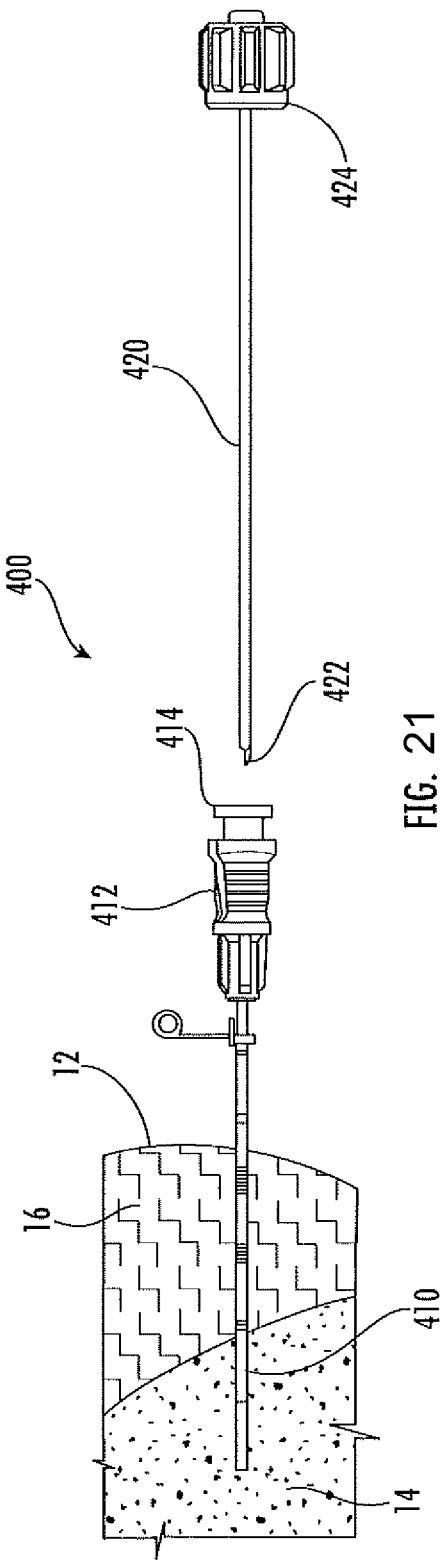

CORE-SEVERING CANNULA FOR BIOPSY DEVICES

CROSS-REFERENCE TO RELATED APPLICATIONS

This application claims priority to U.S. provisional application No. 62/890,512, filed Aug. 22, 2019, the contents of which are herein incorporated by reference in their entirety.

BACKGROUND

1. Field of Invention

The present invention relates to a cannula for use with tissue biopsy devices, and more particularly to a cannula comprising a plurality of flexible fingers for severing a tissue core.

2. Description of the Related Art

Biopsy is a routine medical procedure to excise tissue samples for examination. Some minimally invasive techniques for biopsy procedures involve the use of automatic biopsy coring devices. Such devices typically include one or more hollow needles to cut and retain a sample of tissue, and a handle that includes the mechanism for advancing the needles a fixed distance into the tissue. Examples of biopsy devices using multiple needles are disclosed in U.S. Pat. Nos. 5,655,542, 6,322,523 and US Patent Application Publication No. US 2018/0153525 A1, all of which are herein incorporated by reference in their entireties.

Early core biopsy devices typically use two hollow nested needles, wherein one of needles includes a hook or notch on the side near the distal end, which is used to "grab" the target tissue, while the other needle is advanced to cut a small sample of the target tissue. U.S. Pat. No. 5,320,110 discloses several variations of biopsy needle sets using a method of hooking and cutting tissue. However, all tissue cutting occurs at the side of the needle where the hook is positioned in a knifing action. This tends to result in relatively large samples, and performs no scraping action capable of collecting samples at the cellular level.

An improvement on the conventional needle design utilizes a pincer and cutting needle to obtain a full core of the sample tissue. In such devices, a hollow inner cannula is advanced into the target site to cut a core of the tissue. Subsequently, an outer cannula is advanced distally over the inner cannula. The outer cannula includes a projecting pincer that is dimensioned to fit into a window in the side of the inner cannula. As the outer cannula is advanced, the pincer inserts into the window of the outer cannula, severing the cored tissue sample at its base.

However, while the pincer design results in the collection of more intact core samples, the device is prone to failure. In particular, the pincer is typically a very thin piece of metal that must flex substantially to function. As such, it is subject to high strain and may become permanently deformed or damaged. Furthermore, the pincer must insert accurately into the window at high speed, and any deviation from the intended path can result in catastrophic failure of the device. In addition, the pincer does not completely sever the core from the surrounding tissue. Instead, the pincer typically severs only about 70-80% of the core cross-section, which may result in the core being left attached to the body when the needles are removed. Moreover, even if the sample is successfully removed, it may not be completely intact due to tearing of the tissue near the core of the base. A need therefore exists for an improved full-core biopsy needle set that is less prone to mechanical failure and results in a more complete severing of the core.

SUMMARY OF THE INVENTION

It is therefore an object of the present invention to provide a core-severing cannula comprising a stylet, an inner cutting cannula, and an outer core-severing cannula positioned coaxially with respect to each other, the core-severing cannula having at its distal end a plurality of flexible fingers, the flexible fingers capable of flexing between a first and second position, wherein in the first configuration the flexible fingers are flexed apart sufficiently wide to enable passage of the cutting cannula between them, and wherein in the second configuration the flexible fingers are substantially closed together.

BRIEF DESCRIPTION OF THE DRAWINGS

FIG. 1A is a detail view of the area 1A in FIG. 1.

FIG. 19 is a side plan view of a biopsy device in accordance with the invention.

FIG. 19A is a detail view of the area 19A in FIG. 19.

FIG. 20 is a side plan view of an introducer needle inserted into a biopsy site.

FIG. 21 is a side plan view of the introducer needle of FIG. 20, showing removal of the introducer stylet from the hollow needle.

DETAILED DESCRIPTION OF THE PRESENT INVENTION

Figure 1:
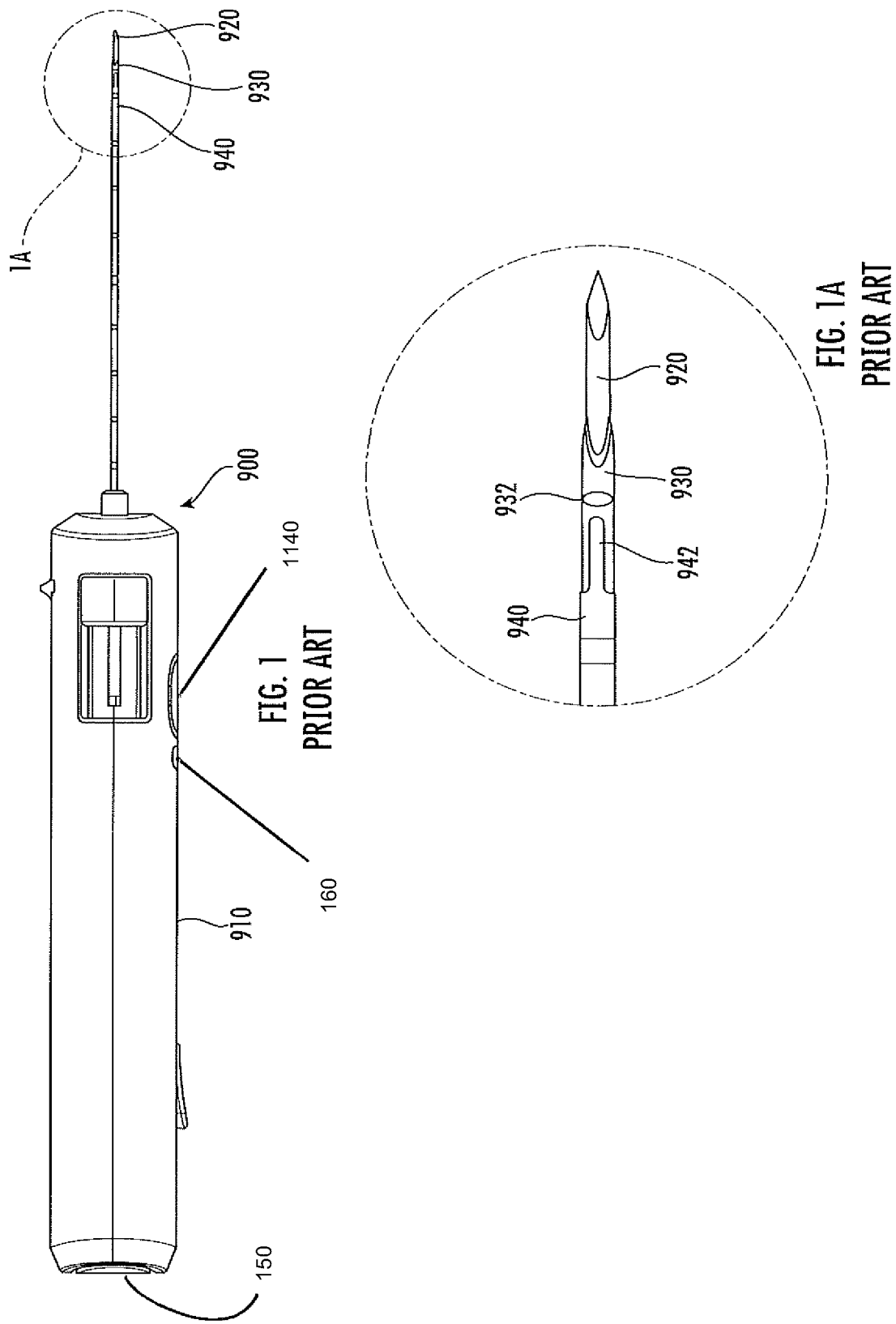
FIG. 1 is a bottom plan view of a prior art biopsy device.

A core-severing needle set 100 according to the present invention is illustrated in FIGS. 19 and 19A and comprises a stylet 130, a core-cutting cannula 110, and a core-severing cannula 120. As used herein, the terms "proximal" and "distal" refer to a user's point of view, with the proximal end being closer to the user and the distal end being closer to the target site 14. "Longitudinal axis" refers to the axis running the length of the device from the proximal end to the distal end. The terms "transverse" and "transversely" refer to a direction substantially orthogonal to a previously described direction. Furthermore, although certain elements are described or depicted as being located on a particular side or end of the device or in a particular orientation, it can be appreciated that some elements may be moved or rotated in different configurations while maintaining the functional relationships of the configurations shown and described below.

The core-severing needle set 100 may be used with an appropriate biopsy device handle. US Patent Application Publication No. US 2018/0153525 A1 discloses one such biopsy device handle, and is herein incorporated by reference in its entirety.

As can be seen in FIG. 1, a prior art biopsy device 900 comprises a handle portion 910, a stylet 920, an inner cannula 930, and an outer cannula 940. The inner 930 and outer 940 cannulas are attached to a two-stage carriage element, described in greater detail below, comprising front and rear portions that are slidable relative to each other a short distance. During insertion of the prior art biopsy needle, the stylet 920 extends beyond the distal ends of the inner 930 and outer 940 cannulas to prevent accidental injury. Once the stylet 920 is located in the appropriate site 14 the user arms the device for activation. The arming step involves retracting the front and rear portions of the carriage element against a biasing component, such as a coil spring.

When the device 900 is activated, the front and rear carriages are biased distally, causing the inner cannula 930 and outer cannula 940 to advanced together distally beyond the distal tip of the stylet 920. As the inner cannula 930 penetrates the tissue 16, the sharp distal end of the inner cannula 930 cuts a core sample away from the target tissue 14. Once the inner cannula 930 has reached its intended depth into the target tissue 14, the front carriage is arrested, and the inner cannula 930 is prevented from further penetration. At this stage, the core remains attached at its base to the target tissue 14. However, the rear carriage continues to advance a short distance, which causes the outer cannula 940 to extend distally relative to the inner cannula 930. As the outer cannula 940 advances, a pincer 942 on the outer cannula 940 inserts into a window 932 formed in the side of the inner cannula 930, severing the core from the target tissue 14 at its base. The pincer 942 remains inserted into the window 932 which retains the core sample within the inner cannula 930. The user then withdraws the entire needle assembly containing the core from the target tissue 14.

Figure 2:
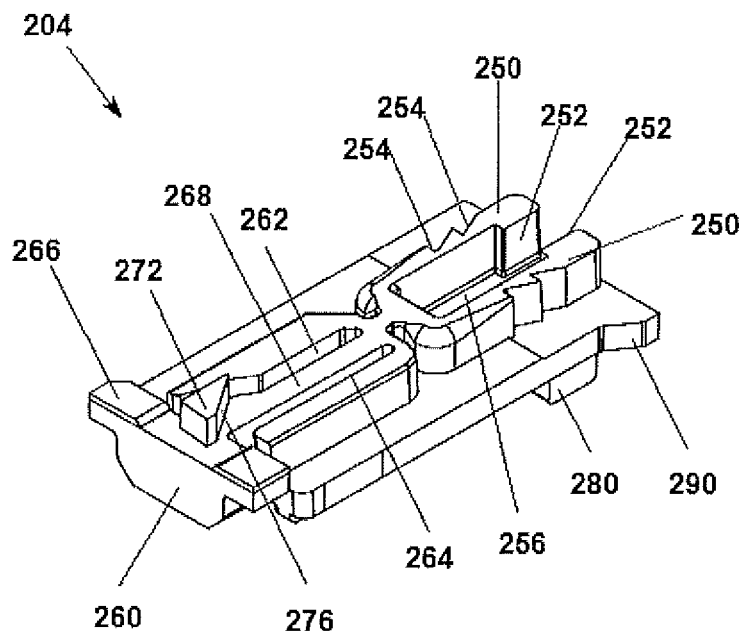
FIG. 2 is a perspective view of the front carriage according to one embodiment of the biopsy device handle of a prior art device.
Figure 3:
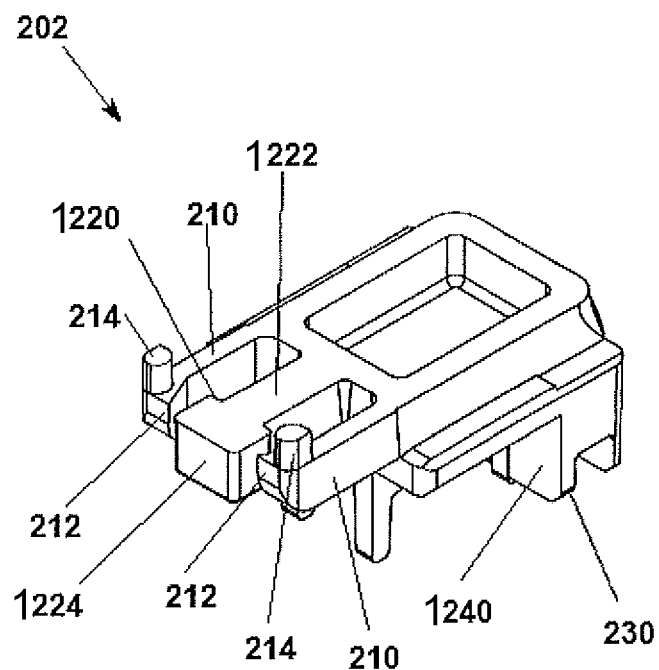
FIG. 3 is a perspective view of the rear carriage according to one embodiment of the biopsy device handle, of the prior art.

FIGS. 2-3, 4A-B, and 5A-B illustrate one embodiment of the carriage assembly 200. The carriage assembly 200 comprises a rear carriage 202 and a front carriage 204. As shown in FIG. 3, the rear carriage 202 includes a pair of prongs 210 extending from a distal end of the rear carriage 202 and a tab 1220 extending between the two prongs 210. The prongs 210 are sufficiently flexible to flex laterally outwardly and away from the tab 1220. Poles 214 project upwardly from the ends of prongs 210. Flanges 230 are formed on opposite sides of the rear carriage 202 and configured to rest upon carriage rails 1110 formed in the housing 1100.

The front carriage 204 includes a pair of tines 250 extending from a proximal end of the front carriage. The tines 250 define a cavity 256 configured to receive the tab 1220. In at least one embodiment, illustrated in FIG. 2, the tab 1220 includes a stem 1222 and a head 1224 wider than the stem 1222. The tines 250 are spaced apart approximately the width of the head 1224, and include inwardly facing tips 252 defining a space approximately the width of the stem 1222. As the front carriage 204 and rear carriage 202 are joined, the tab 1220 is inserted between the tines 250. Once the head 1224 has been inserted past the tips 252, the tab 1220 is secured. The front carriage 204 also includes a pair of flanges 280 formed on opposite sides and configured to rest upon the carriage rails 1110.

Figure 4A:
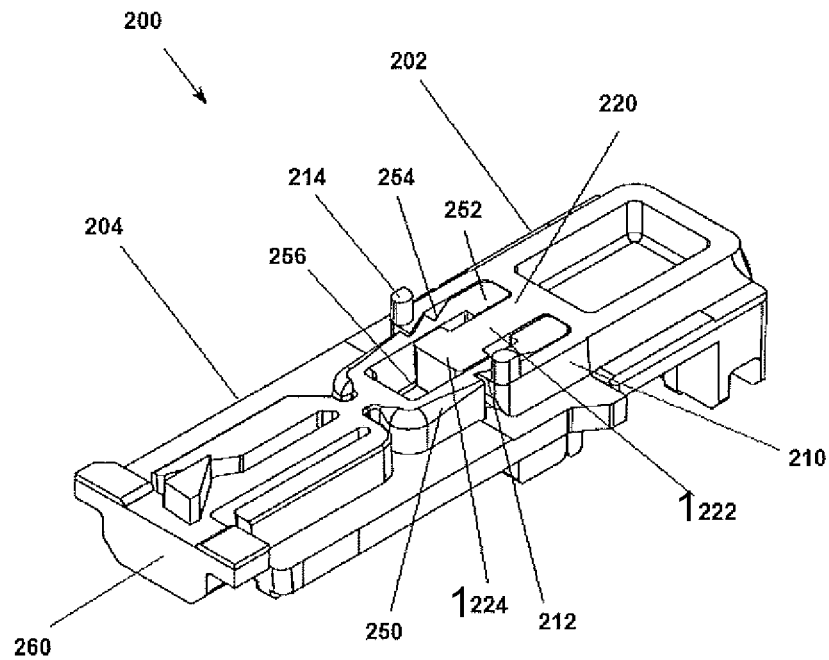
FIG. 4A is a perspective view of the prior art carriages of FIGS. 2-3, showing the carriages assembled in a charged state.
Figure 4B:
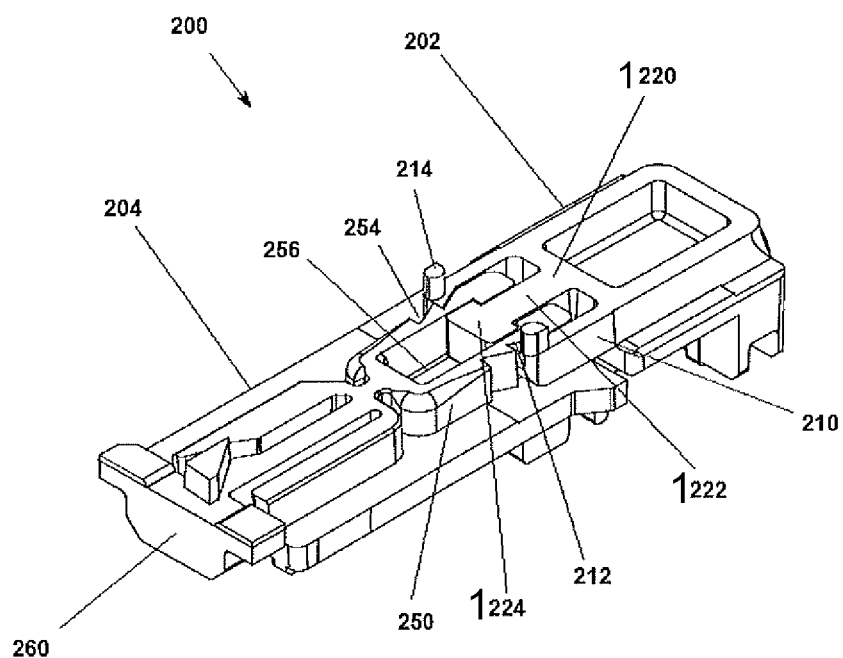
FIG. 4B is a perspective view of the prior art carriages of FIGS. 2-3, showing the carriages assembled in an discharged state.
Figure 5A:
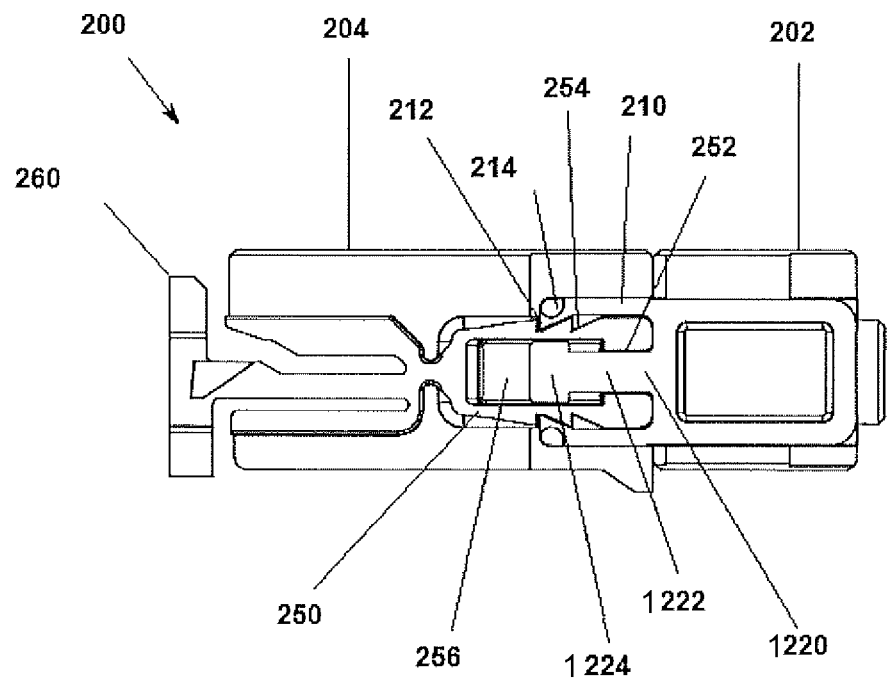
FIG. 5A is a top view of the prior art carriage assembly of FIG. 4A.
Figure 5B:
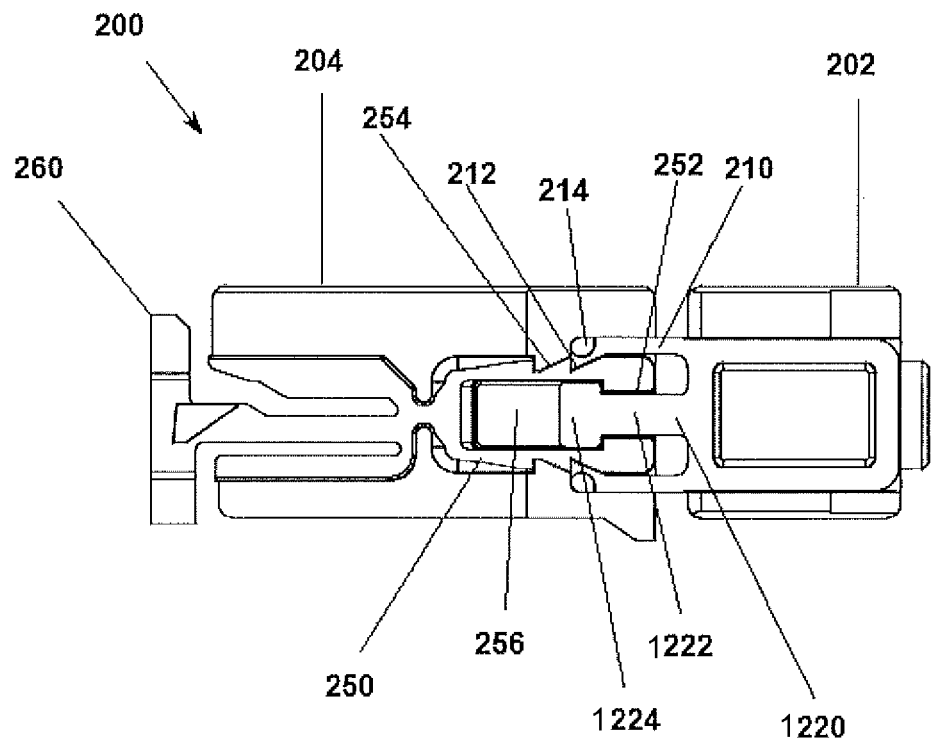
FIG. 5B is a top view of the prior art carriage assembly of FIG. 4B.

In at least one embodiment, the cavity 256 is longer than the head 1224, enabling the rear carriage 202 to slide relative to the front carriage 204 while the two pieces are mated, as illustrated in FIGS. 4A-B. In this embodiment, prongs 210 are coplanar with the tines 250, but are partially overlapping the tines 250 when viewed from the top of the device, as shown in FIGS. 5A-B. The tines 250 also include a plurality of serrations 254 along their outer edges. Each of the prongs 210 also includes an inward-facing projection 212, which extends sufficiently to engage the serrations 254. As the tab 1220 is moved within the cavity 256 while the front carriage 204 and rear carriage 202 are mated, the prongs 210 are flexed outward slightly, and the projections 212 slide across the serrations 254. Preferably, the serrations 254 are generally triangular in shape, having a steeper slope on the distal side than on the proximal side. In the preferred embodiment, the asymmetrical slope of the serrations 254 require less force to pull the rear carriage 202 and front carriage 204 apart than it does to push them together, providing a ratcheting effect.

During arming of the device, the mated rear carriage 202 and front carriage 204 are pulled proximally against the first biasing element 1400. The first biasing element 1400 is preferably a helical spring, although other compressible spring-like elements are within the scope of the invention. In at least one embodiment, the first biasing element extends between a biasing wall 170 near a proximal end of the housing 1100 and a proximal face of the rear carriage 202. In other embodiments, the first biasing element 1400 may extend between the biasing wall 170 and the front carriage 204. In still further embodiments, the first biasing element 1400 may surround a portion of the needle assembly 800.

During the arming process, the prongs 210 are flexed apart to allow the projections 212 to pass over the steep inclines of the serrations 254 and bring the carriages 202, 204 together. In at least one embodiment, the prongs 210 are forced apart as a pair of inclines 338 are advanced between the poles 214. When the front carriage 204 and rear carriage 202 are brought together, the carriage assembly 200 is in a charged state.

When the device is fired, both carriages 202, 204 move together in a distal direction until a distal face 1240 of the rear carriage 202 impacts an end face 614. As shown in FIGS. 13A-B and 14A-B, the front carriage 204 travels a short distance relative to the rear carriage 202 as the tab 1220 moves within the cavity 256 and the serrations 254 are moved relative to the projections 212, transitioning to a discharged state. Preferably, the embodiment of the device shown in FIGS. 13A-B and 14A-B is used with a nested needle assembly 800, where different portions of the needle assembly 800 are attached to the front carriage 204 and rear carriage 202 to allow the portions of the needle assembly 800 to move relative to each other.

In some embodiments, the end face 614 is movable to adjust the depth of penetration of the device. In the embodiment shown in FIGS. 13A-B and 14A-B, a stroke adjuster 600 comprises a main body and a slider 620 attached to the bottom surface of the main body by a neck 630. A pair of arresting arms 612 extend proximally from the main body and each include an end face 614. The main body is disposed inside the housing 1100, and the neck 630 extends downward through a longitudinal slot 1120 formed in a bottom surface of the housing 1100. On each side of the longitudinal slot 1120, the interior surface of the housing 1100 is provided with a plurality of ramps 1130 in a row extending away from the interior surface. The main body may include a pair of skids 616 projecting downwardly and configured to engage the ramps 1130. The ramps 1130 are configured to resist longitudinal movement of the skids 616 in the distal direction.

Preferably, the ramps 1130 are inclined more steeply on the proximal side than on the distal side. An upwardly transverse force may be applied to the slider 620 to lift the skids 616 clear of the ramps 1130 and enable the stroke adjuster 600 to be manipulated longitudinally.

In one embodiment, the housing 1100 is provided with three pairs of ramps 1130 defining three adjustable positions. However, other numbers of ramps 1130 may be used to define the desired number of adjustable positions. The numbers of necks 630, longitudinal slots 1120, and rows of ramps 1130 may be modified without departing from the scope of the invention; for example, the housing may be provided with a single row of ramps and a longitudinal slot on each side of the ramps, and the stroke adjustor may be provided with two necks, each neck extending through one of the longitudinal slots.

Figure 13A:
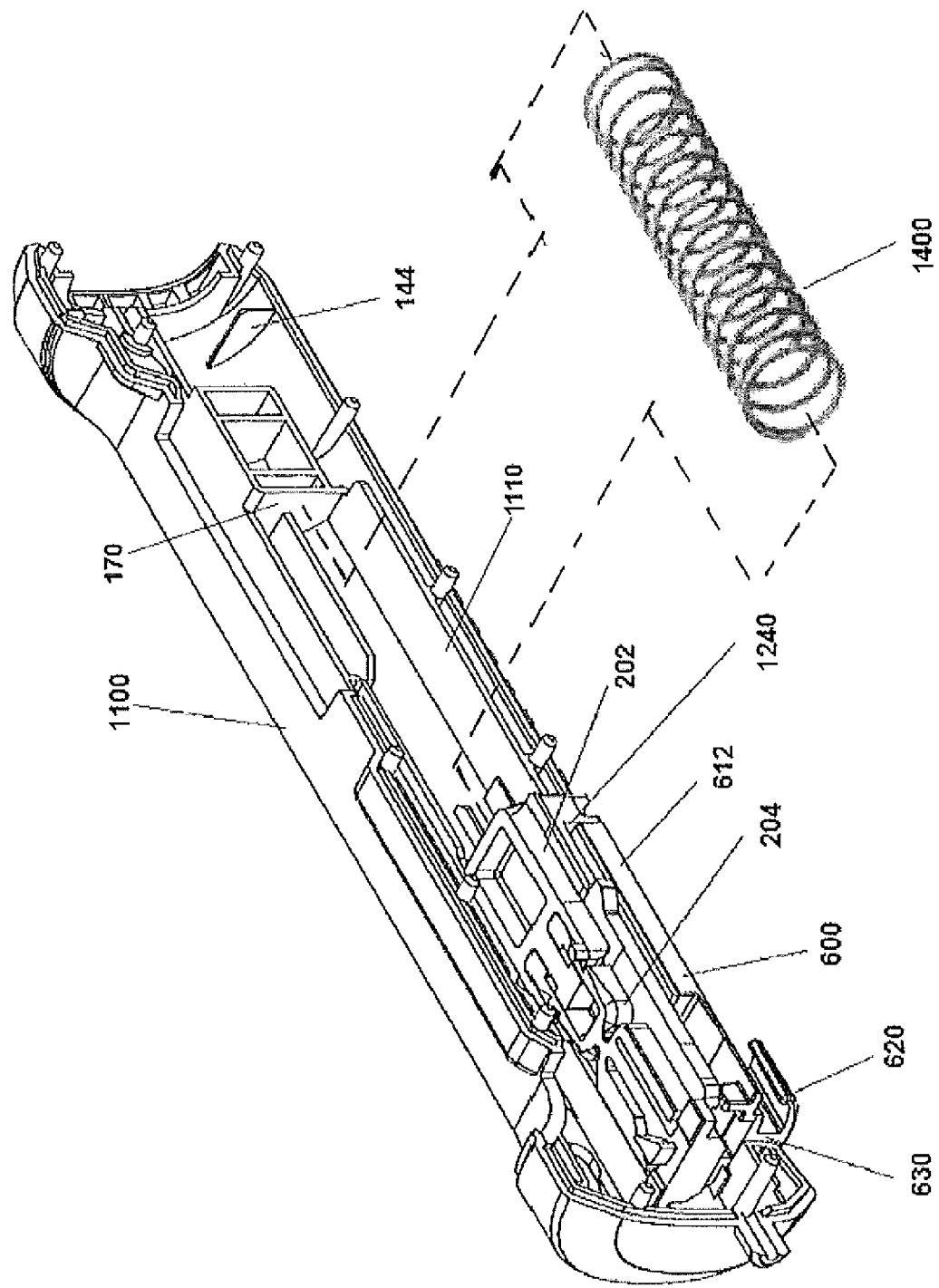
FIG. 13A is a perspective view of the carriage assembly, stroke adjuster, and the right half of the housing according to one embodiment of the prior art, showing the stroke adjuster in a first position and the carriage assembly in a charged state.
Figure 13B:
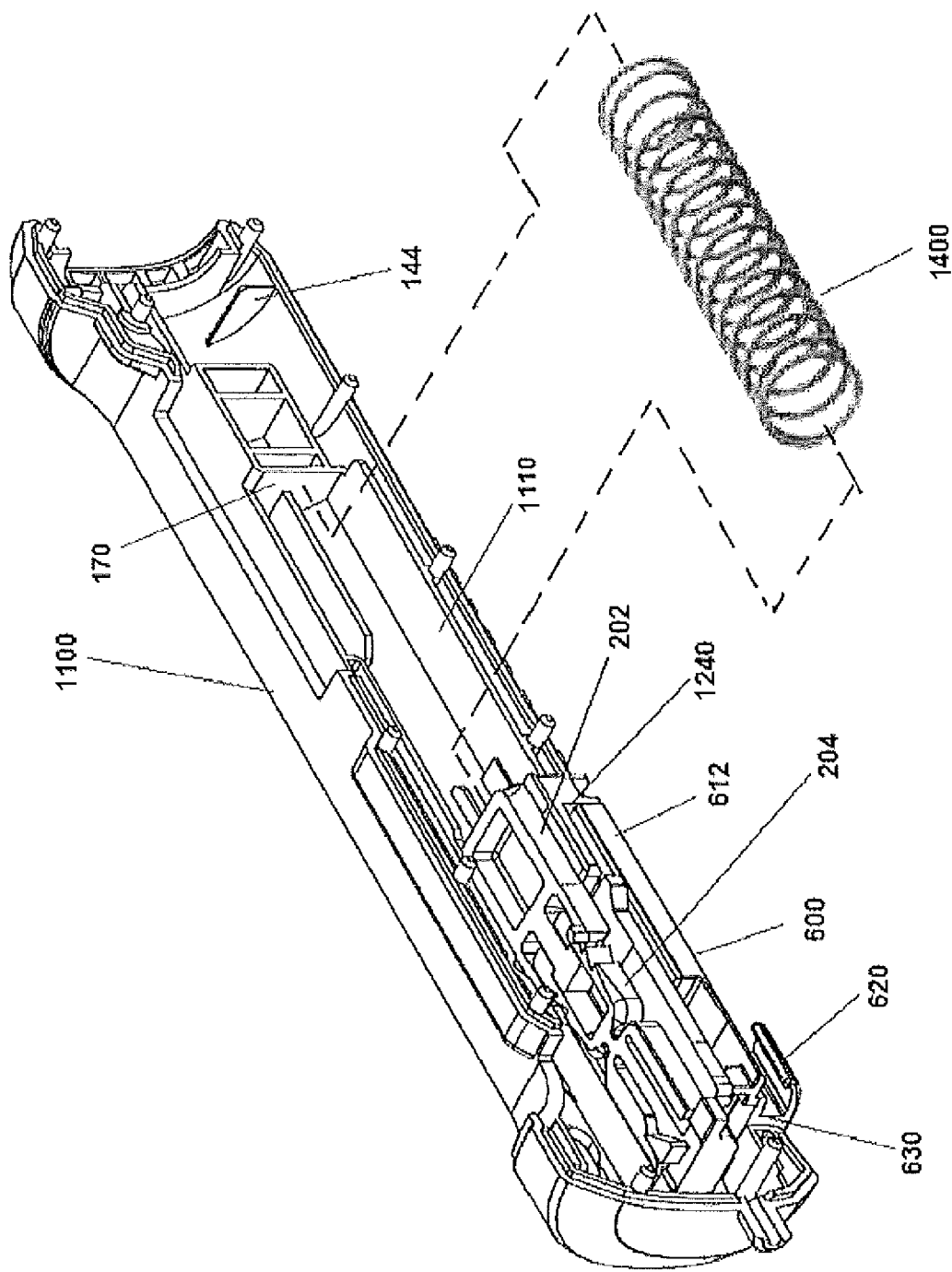
FIG. 13B is a perspective view of the prior art carriage assembly, stroke adjuster, and the right half of the housing of FIG. 13A, showing the stroke adjuster in a first position and the carriage assembly in a discharged state.
Figure 14A:
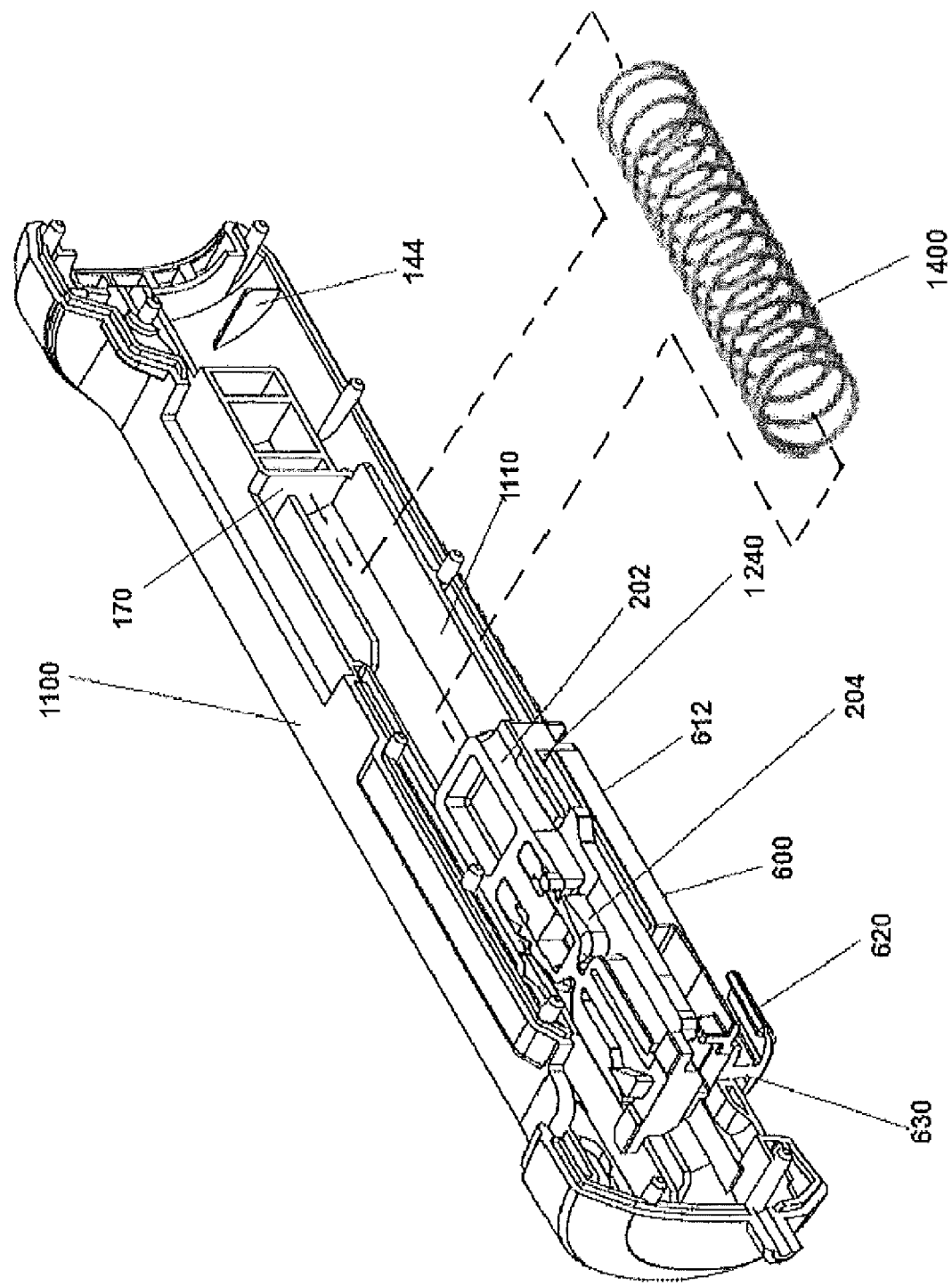
FIG. 14A is a perspective view of the prior art carriage assembly, stroke adjuster, and the right half of the housing of FIG. 13A, showing the stroke adjuster in a second position and the carriage assembly in a charged state.
Figure 14B:
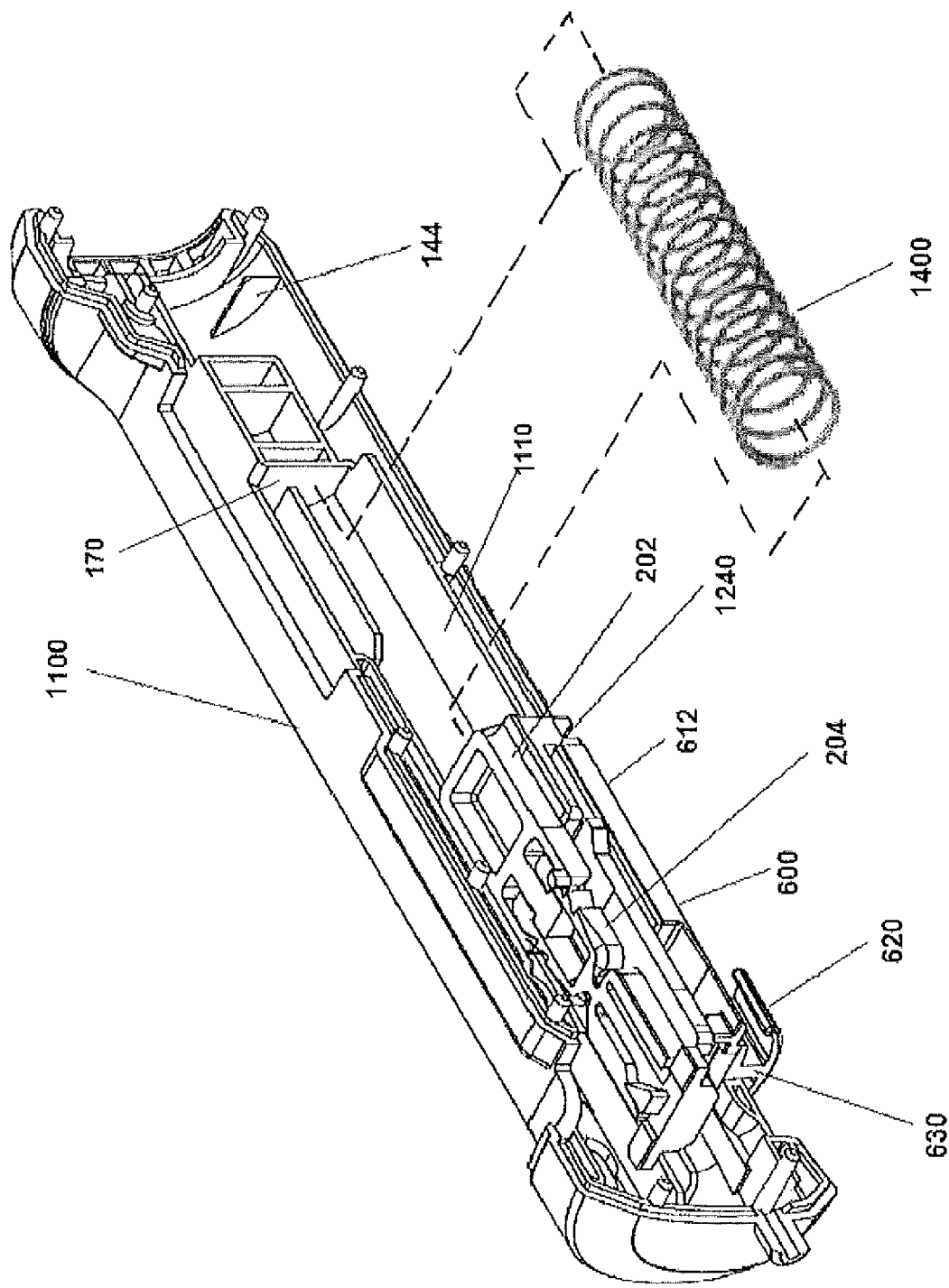
FIG. 14B is a perspective view of the prior art carriage assembly, stroke adjuster, and the right half of the housing of FIG. 13A, showing the stroke adjuster in a second position and the carriage assembly in a discharged state.

As the device is fired, the carriage assembly 200 is forced to the distal end of the housing 1100. As the distal face 1240 of the rear carriage 202 impacts the end face 614 at the end of the arresting arms 612, the rear carriage 202 is arrested. The ramps 1130 are configured to be sufficiently steep to prevent the skids 616 from slipping against the ramps 1130 due to the impact force of the rear carriage 202 contacting the end face 614. FIGS. 13A-B show the stroke adjuster positioned between the first ramp and the end of the housing 1100. FIGS. 14A-B show the stroke adjuster 600 positioned between the first ramp and second ramp. Since the stroke adjuster 600 is movable between a plurality of positions, the distance traveled by the carriage assembly 200 is thereby also adjusted accordingly. In embodiments where a needle cannula is fixed to the one or both carriages 202, 204, the depth of penetration is thereby also adjusted.

Figure 17:
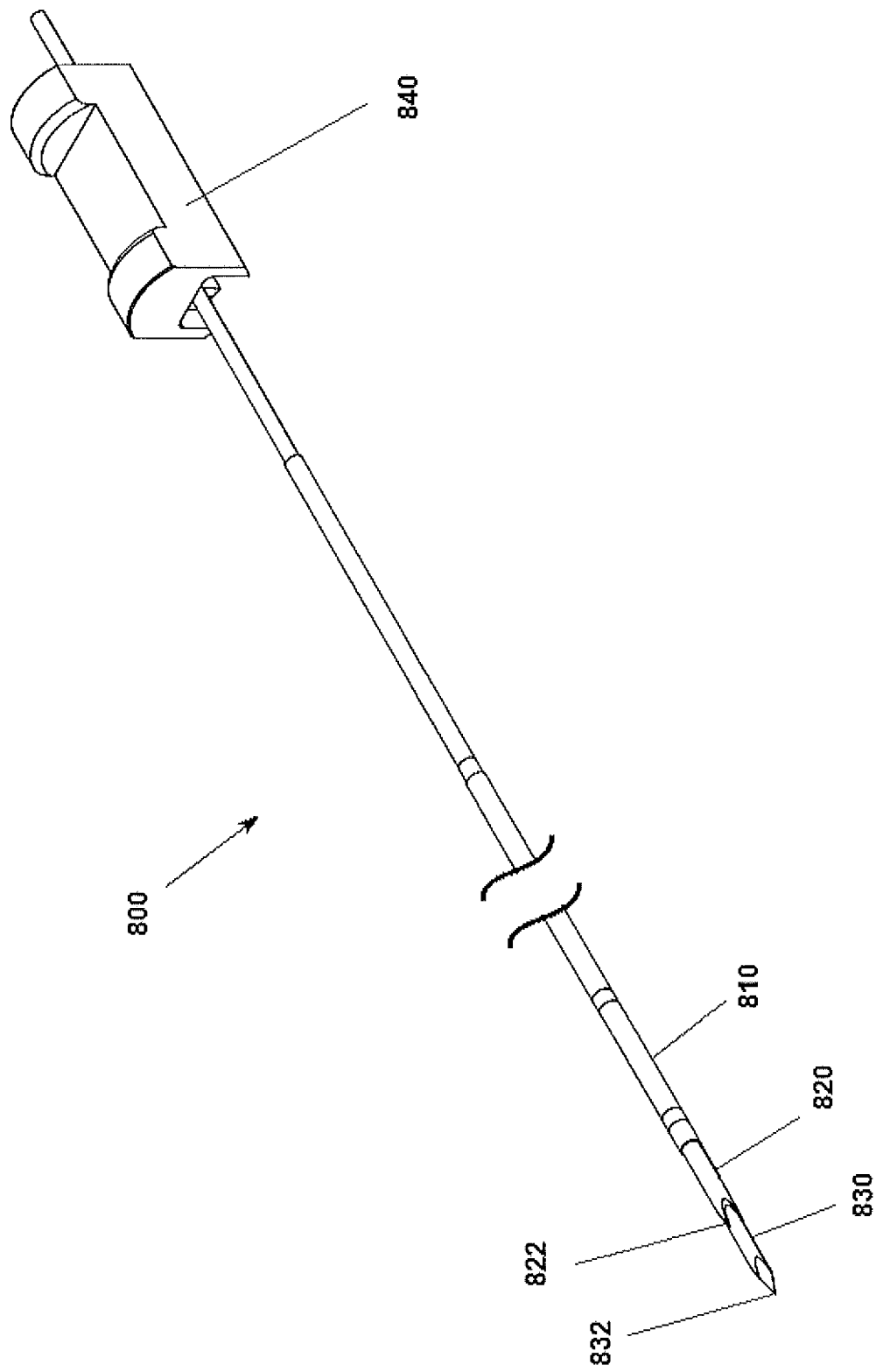
FIG. 17 is a perspective view of one embodiment of the needle assembly of the prior art.
Figure 18:
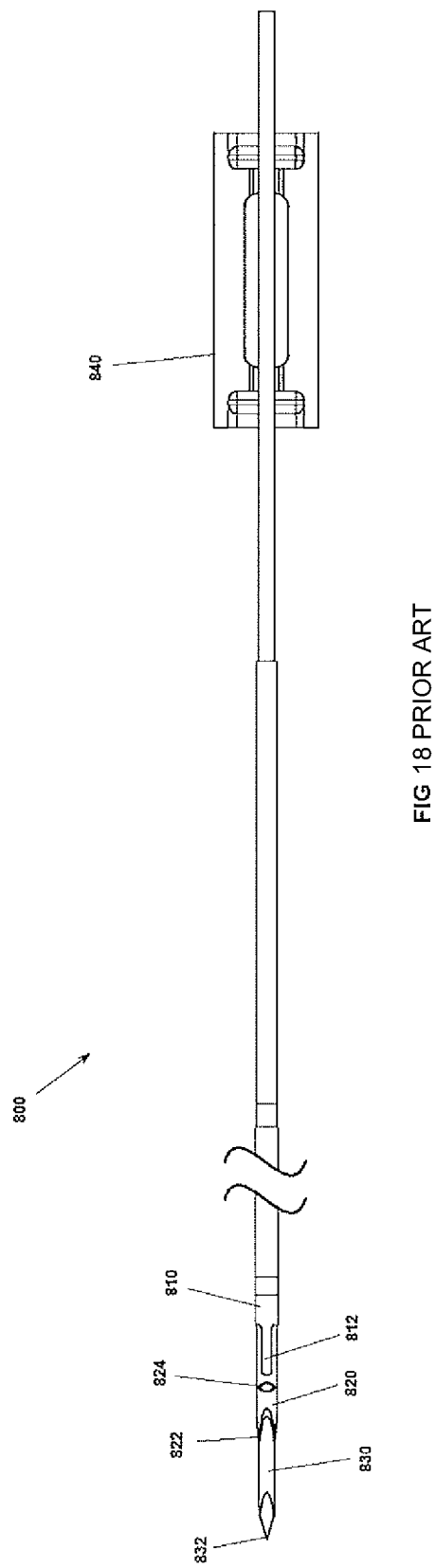
FIG. 18 is a bottom view of the needle assembly of FIG. 17.
Figure 22:
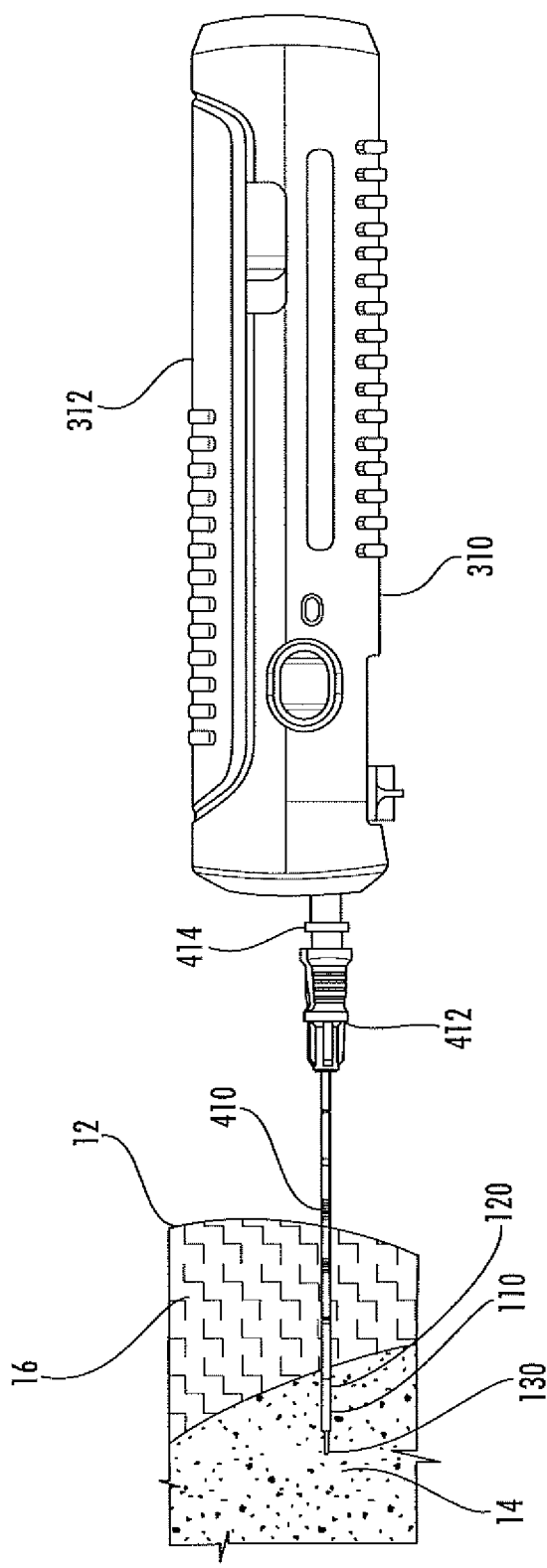
FIG. 22 is a side plan view of a biopsy device in accordance with the invention after insertion into the hollow needle of FIG. 21.

In some embodiments, the needle assembly 800 comprises an outer cannula 810, an inner cannula 820, and a stylet 830 positioned coaxially, for example the needle as disclosed in U.S. Pat. No. 5,655,542. FIGS. 17-18 illustrate a multiple-cannula needle according to one embodiment of the present invention. The stylet 830 terminates in a sharp tip 832. The inner cannula 820 surrounds and is coaxial with the stylet 830. The inner cannula 820 terminates in a cutting tip 822 to cut a generally cylindrical sample of tissue. As shown in FIG. 18, the inner cannula 820 also includes an opening 824 proximal to the tip 822. The outer cannula 810 surrounds and is coaxial with the inner cannula 820. A finger 812 extends distally from the end of the outer cannula 810 and is angled toward the longitudinal axis. The finger 812 has a width less than the width of the opening 824. In this embodiment, the stylet 830 does not move with respect to the housing 1100. Preferably, a proximal end of the stylet 830 is secured in a clump 840, which rests in a groove in the housing 1100. The inner cannula 820 is fixed to the rear carriage 202. The outer cannula 810 is fixed to the front carriage 204.

During insertion of the needle, the innermost stylet 830 is extended beyond the tips of the inner cannula 820 and outer cannula 810. When the device is activated, the inner cannula 820 and outer cannula 810 are advanced together distally beyond the tip of the stylet 830. As the inner cannula 820 penetrates the tissue, the cutting tip 822 cores a sample of tissue. Once the inner cannula 820 has reached the intended depth into the tissue, the inner cannula 820 is prevented from further penetrating the tissue. When used with the carriage assembly 200 shown in FIGS. 13A-B and 14A-B, the cutting depth is reached when the rear carriage 202 contacts the end face 614. The outer cannula 810 continues to travel a short distance with respect to the inner cannula 820 as the front carriage 204 transitions to the discharged state. As the outer cannula 810 advances, the finger 812 inserts into the opening 824 of the inner cannula 820 to cut the tissue sample transversely. Because the finger 812 remains inserted into the end of the inner cannula 820, the tissue sample is retained in the inner cannula 820, and the entire needle assembly 800 is withdrawn.

Although a needle assembly having two cannulas is preferred, some embodiments may use other types of needles including single cannula needles. In those embodiments, the carriage assembly 200 may comprise only a single carriage. A single carriage design does not become charged or discharged because there are no moving parts. Accordingly, the single carriage may omit features facilitating charging and discharging such as the prongs 210, the tab 1220, and the tines 250.

Figure 6:
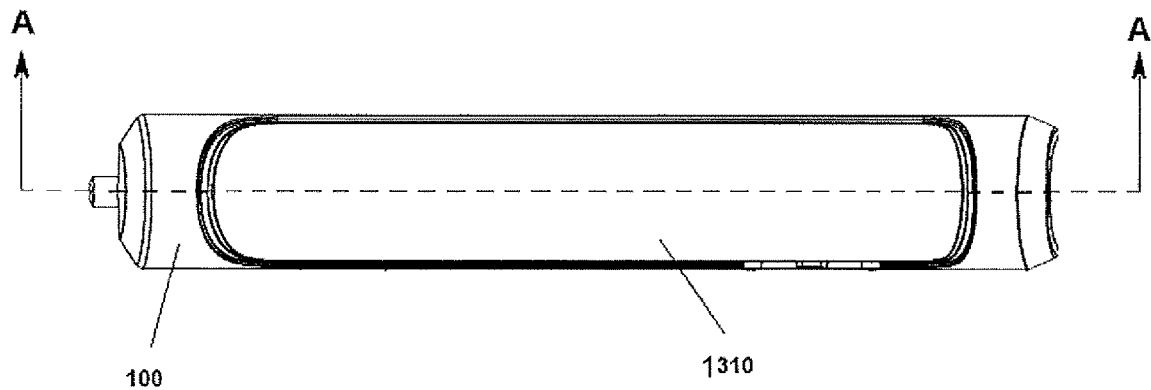
FIG. 6 is a top view of the lever assembly and housing according to one embodiment of the prior art biopsy device handle in a closed position.
Figure 6A:
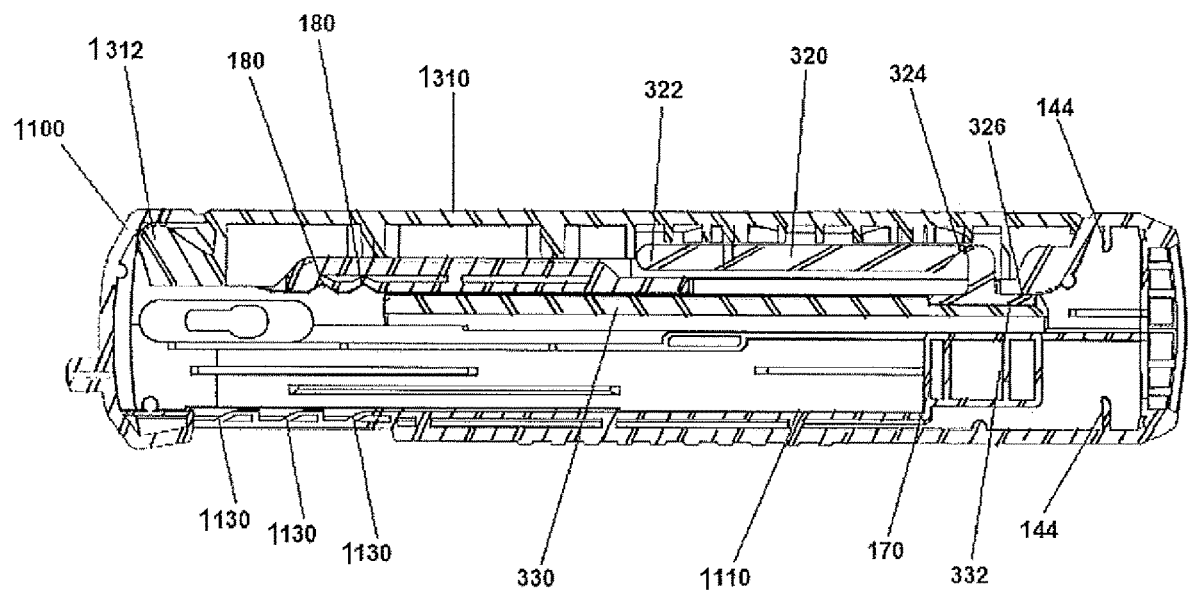
FIG. 6A is a cross-sectional view along lines A-A in FIG. 6.
Figure 7:
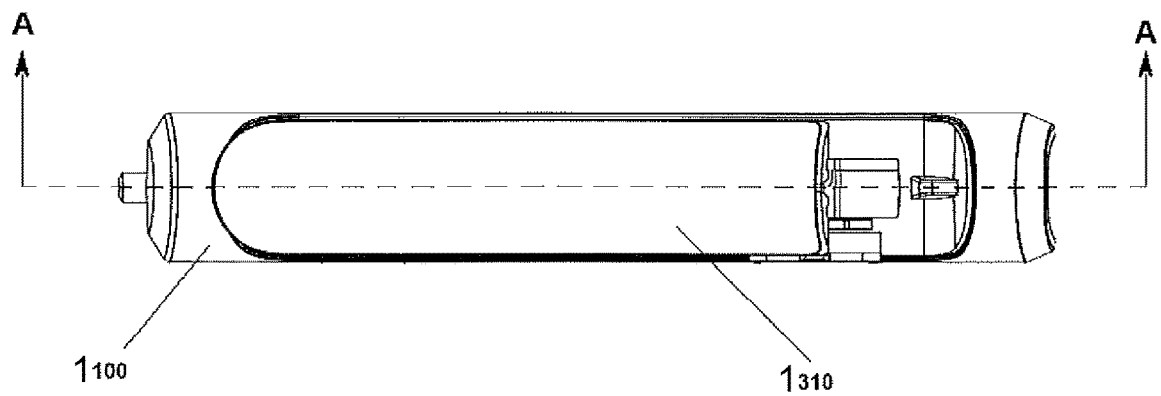
FIG. 7 is a top view of the lever assembly and housing of FIG. 6 in an open position.
Figure 7A:
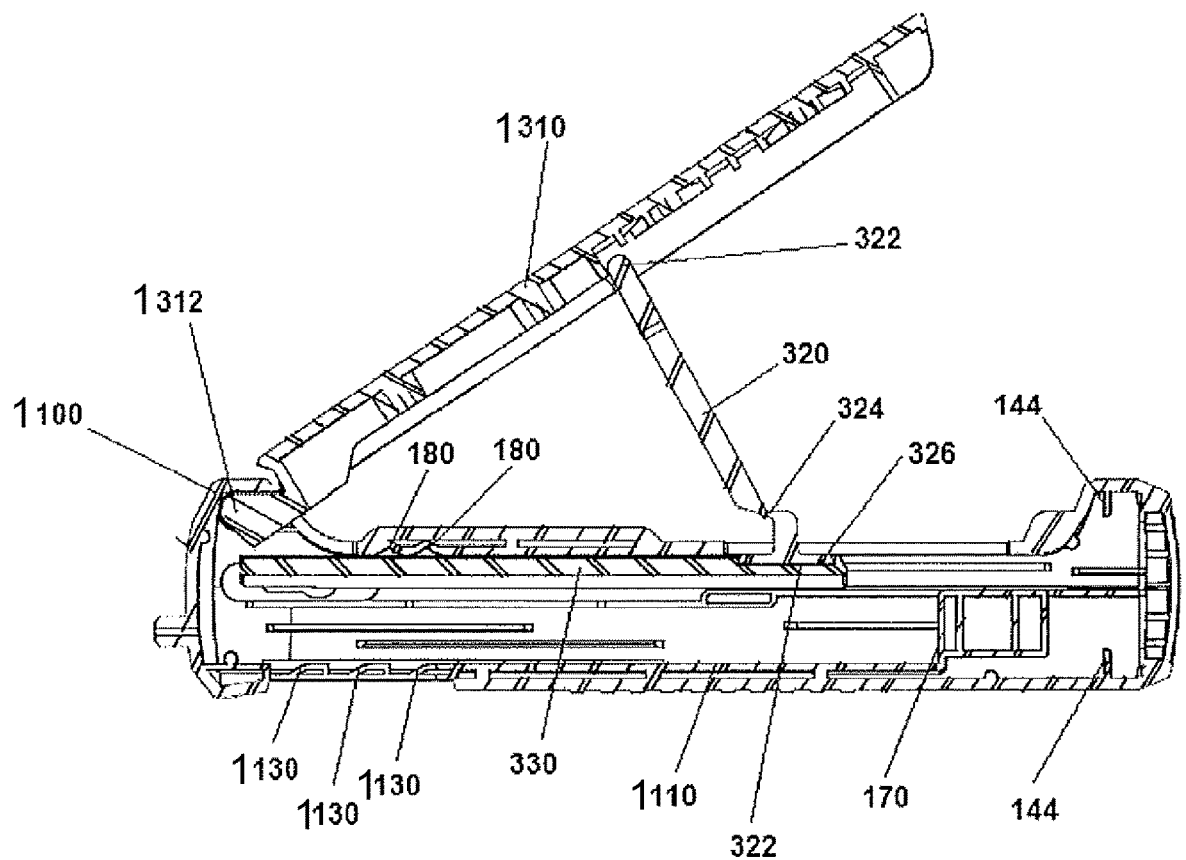
FIG. 7A is a cross-sectional view along lines A-A in FIG. 7.
Figure 8:
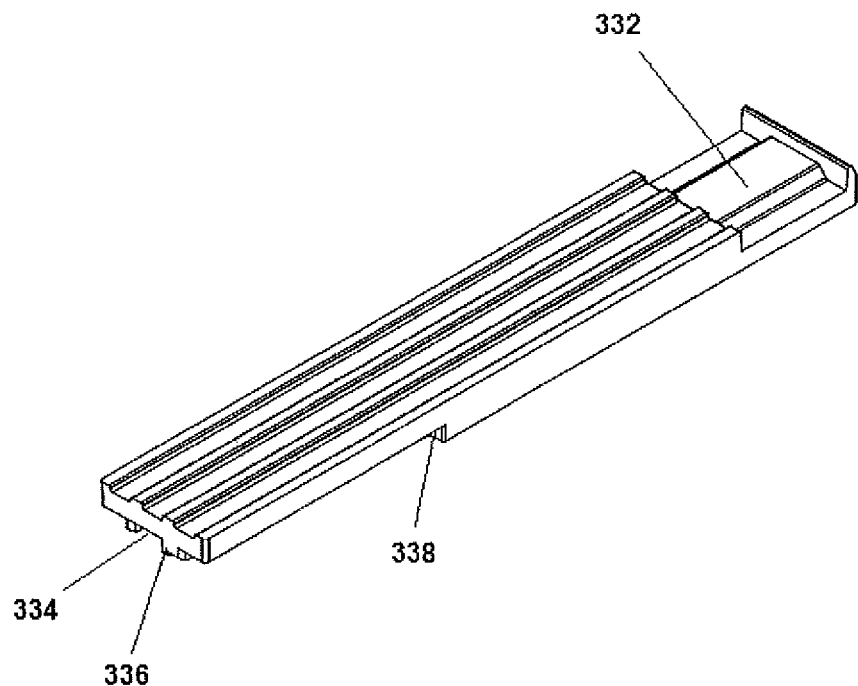
FIG. 8 is a perspective view of the catcher according to one embodiment of the prior art biopsy device handle.
Figure 9:
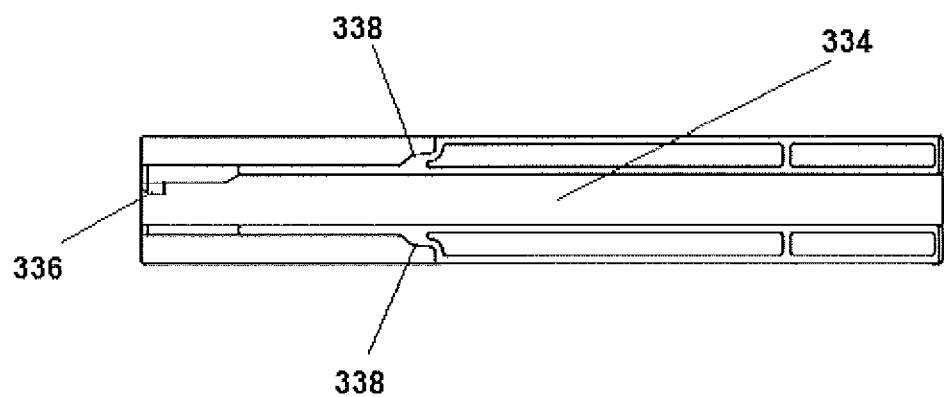
FIG. 9 is a bottom view of the catcher of FIG. 8.
Figure 10:
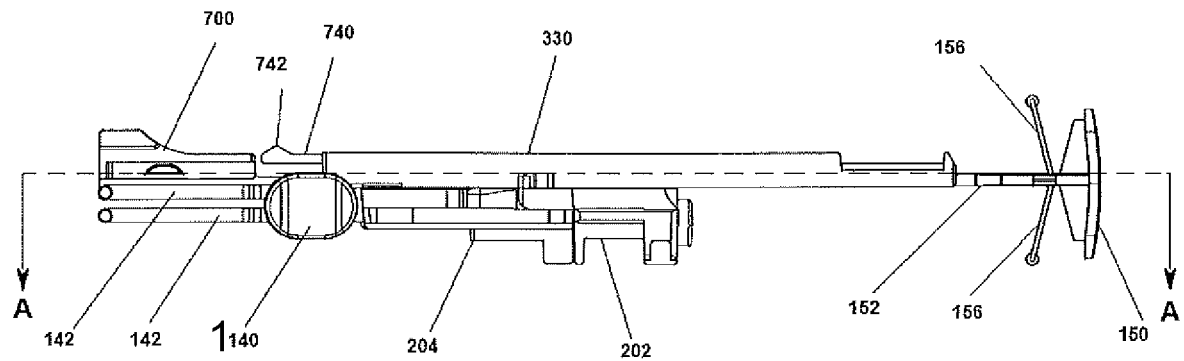
FIG. 10 is a right side view of the carriage assembly, catcher, side trigger, rear trigger, and safety according to one embodiment of the prior art, showing the safety in a locked position.
Figure 10A:
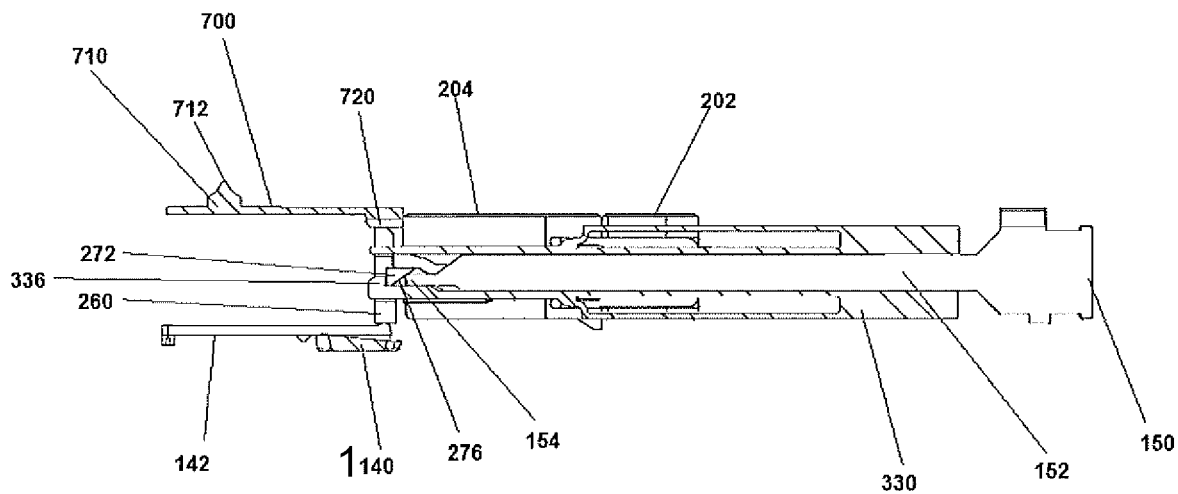
FIG. 10A is a cross-sectional view along lines A-A in FIG. 10.

In order to prepare the device for activation, the carriage assembly 200 is withdrawn proximally against the first biasing element 1400 using the lever assembly 1300. As shown in FIGS. 6A and 7A, the lever assembly 1300 comprises a lever 1310, a linkage 320, and a catcher 330. The lever 1310 is attached to the housing 1100 by a first hinged connection 1312 at the distal end. Preferably the first hinged connection 1312 is a T-shaped hinge, however other types of hinges may be used. The linkage 320 is attached to the lever 1310 by a second hinged connection 322 near the middle of the lever 1310 and extends proximally. Preferably the second hinged connection 322 is also a T-shaped hinge, however types of hinges may be used. The linkage 320 includes a foot 326 attached to the main body of the linkage by a third hinged connection 324. The third hinged connection 324 is preferably a living hinge, although other types of hinges are within the scope of the invention.

The catcher 330 includes a footplate 332 in the top surface of the catcher 330 at a proximal end, which is configured to seat the foot 326. A shallow longitudinal channel 334 is formed in a bottom surface of the catcher 330 to a first depth. At a distal end of the catcher 330, a transversely projecting catch 336 extends from a side wall of the channel 334.

Figure 11:
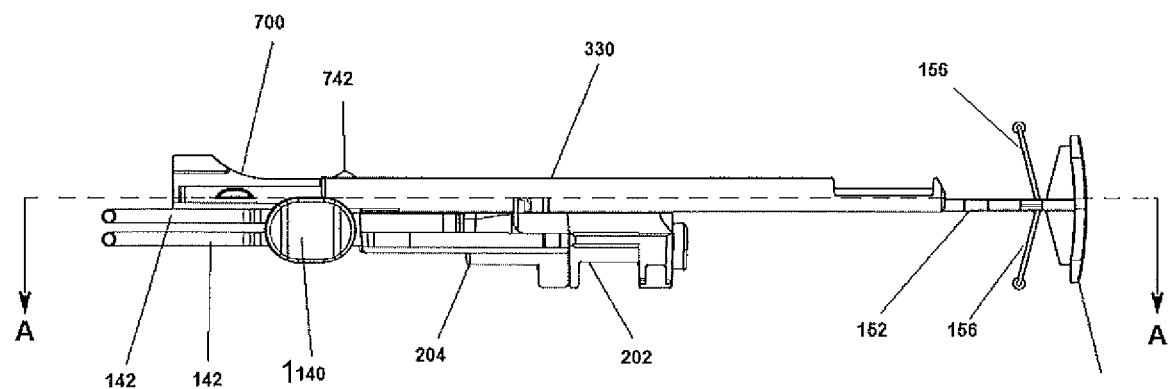
FIG. 11 is a right side view of the prior art carriage assembly, catcher, side trigger, rear trigger, and safety of FIG. 10, showing the safety in an unlocked position.
Figure 11A:
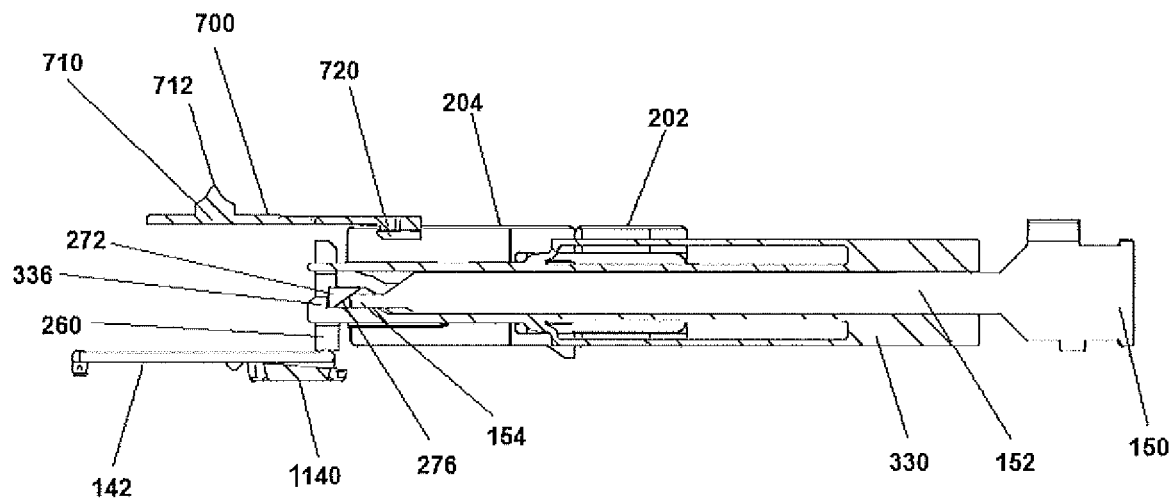
FIG. 11A is a cross-sectional view along lines A-A in FIG. 11.
Figure 11B:
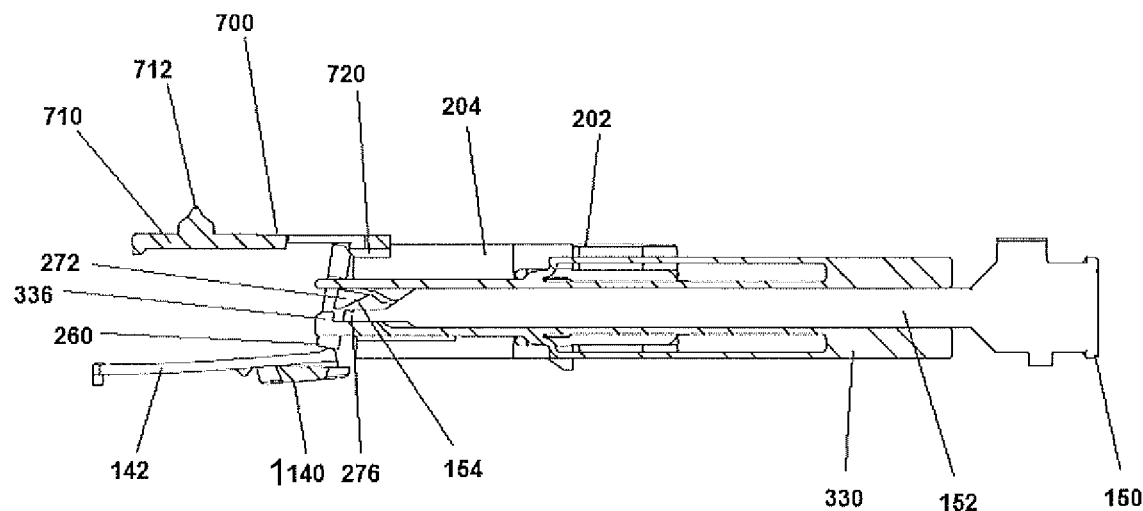
FIG. 11B is the cross-section view of FIG. 11A, showing the device being fired by depressing the side button.
Figure 11C:
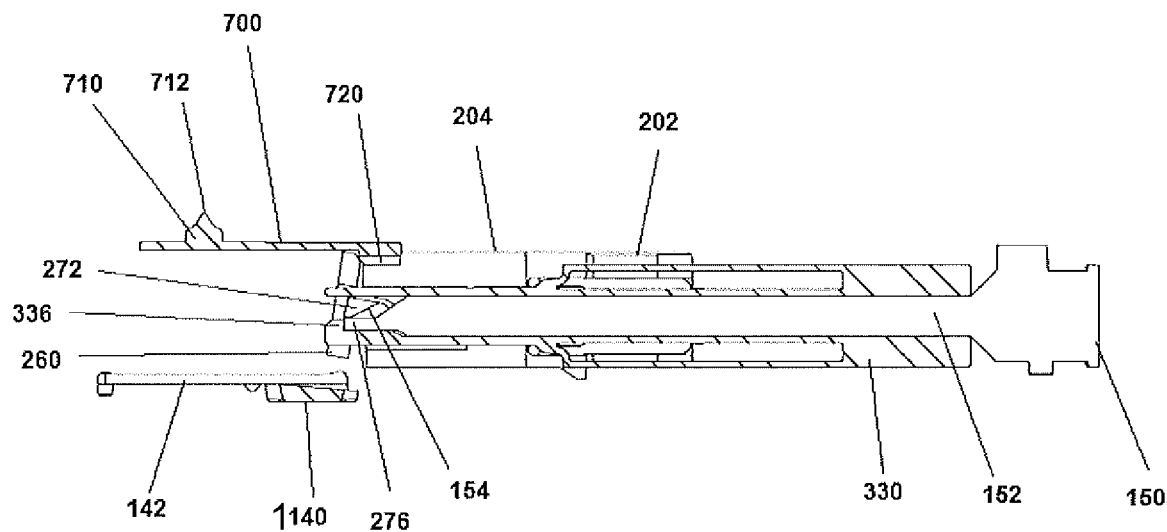
FIG. 11C is the cross-section view of FIG. 11A, showing the device being fired by depressing the rear button.
Figure 12:
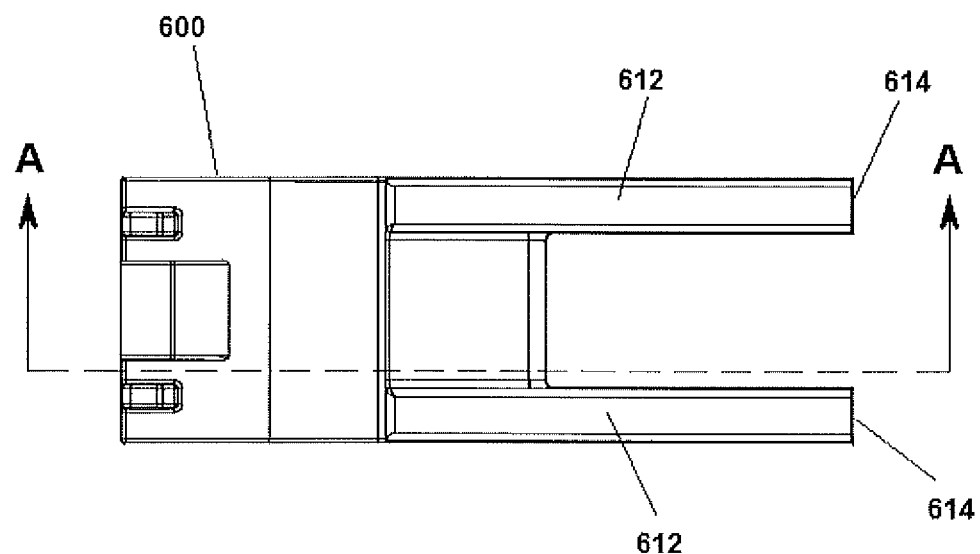
FIG. 12 is a top view of the stroke adjuster according to one embodiment of the prior art.
Figure 12A:
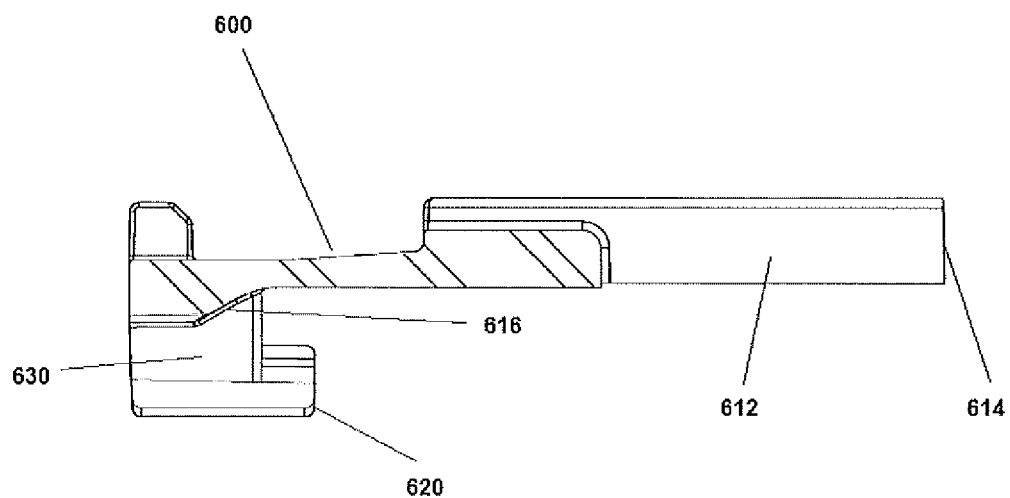
FIG. 12A is a cross-sectional view along lines A-A in FIG. 12.

As shown in FIG. 2, the front carriage 204 includes a deflecting portion 260 extending proximally from the main body of the front carriage 204. The deflecting portion 260 may be integral with the main body of the front carriage 204, and defined by cutouts 262, 264 on either side of the deflecting portion 260. In a neutral position, the deflecting portion 260 is substantially aligned with the longitudinal axis, as shown in FIG. 11A. In a deflected position, the deflecting portion 260 is flexed at an angle to the longitudinal axis, as shown in FIGS. 11B and 11C.

In the embodiment shown in FIG. 2, the deflecting portion 260 is generally T-shaped and comprises a bar 266 and a flexible beam 268. The flexible beam 268 may be asymmetrical with respect to the longitudinal axis, in order to provide greater deflection in one direction than in the other. In a preferred embodiment, the deflecting portion 260 deflects toward cutout 262 and away from cutout 264. In that embodiment, cutout 262 is preferably wider at the distal end to accommodate the deflecting portion 260 as it is deflected transversely.

The deflecting portion 260 is further provided with a post 272 extending upwardly. The post 272 has a width less than the width of the channel 334 and is configured to fit within the channel 334 when the catcher 330 is placed on top of the front carriage 204. Preferably, the height of the post 272 is less than or equal to the first depth of the channel 334.

FIGS. 6A and 7A show movement of the lever assembly 1300. Prior to arming the device, the catcher 330 is positioned proximally relative to the front carriage 204. The carriage assembly 200 is omitted from FIGS. 6A and 7A in order to provide a clearer view of the lever assembly 1300 relative to the housing 1100. When the lever 1310 is lifted, the linkage 320 is forced to pivot and drive the foot 326 distally. Because the foot 326 rests on the footplate 332 of the catcher 330, the distal motion also causes the catcher 330 to slide distally inside of the housing 1100. As the catcher 330 is advanced distally over the front carriage 204, the post 272 is slidably received within the channel 334. With the deflecting portion 260 of the front carriage 204 in the neutral position, the catch 336 overlaps at least a portion of the post 272, preventing the front carriage 204 from sliding distally with respect to the catcher 330.

As the lever 1310 is closed, the pivot of the linkage 320 is reversed, causing the catcher 330 to slide proximally with respect to the housing 1100. Because the catch 336 retains the post 272, the retraction of the catcher 330 also causes the carriage assembly 200 to be retracted, compressing the first biasing element 1400. When the lever 1310 is completely closed, the catcher 330 and carriage assembly 200 are completely retracted, and the device is in an armed state.

To fire the armed device, the deflecting portion 260 of the front carriage 204 is moved from the neutral position to the deflected position, wherein the post 272 is moved out of longitudinal alignment with the catch 336 as shown in FIGS. 11B and 11C. When the post 272 is misaligned, the catch 336 no longer retains the post 272, and the carriage assembly 200 is free to slide distally with respect to the catcher 330 as the first biasing element 1400 decompresses. In at least one embodiment, the width of the post 272 is less than or equal to the width of the channel 334 minus the width of the catch 336, such that the post 272 may pass through the space formed by the catch 336 and channel 334. When the post 272 has advanced distally past the catch 336, the beam 268 unflexes and the deflecting portion 260 returns to the neutral position.

It can be appreciated in alternative embodiments that the beam 268 may be oriented at an angle to the longitudinal axis in the neutral position. In those embodiments, the catch 336 still overlaps the post 272 in the neutral position in a longitudinal direction, the post 272 is deflected into the channel and away from the catch 335 when in the deflected position.

To move from the neutral position to the deflected position, the deflecting portion is provided with a transverse face and an inclined face 276. The transverse face is substantially parallel to the longitudinal axis of the device. When a transverse force is applied to the transverse face, the beam 268 bends generally in the direction of the transverse force. A side button 1140 may be disposed in a side of the housing 1100 and is depressible into the device to apply a transverse force to the transverse face as shown in FIG. 11B. In other embodiments, the transverse force may be applied by a different activating element, such as a switch or slide. In still further embodiments, the housing 1100 may simply include an opening through which a user may directly apply a transverse force to the transverse face using a finger or tool. The side button 1140 may be attached to an interior wall of the housing 1100 by a pair of flexible arms 142 to provide resiliency. In other embodiments, the side button 1140 may include a biasing means, such as a helical spring, disposed between the side button 1140 and the interior of the housing 1100 to provide resiliency.

The inclined face 276 is located on the post 272 and is angled between the longitudinal and lateral axes. When a longitudinal force is applied to the inclined face 276, the beam 268 bends away from the longitudinal axis. In the embodiment illustrated in FIG. 11C, the force is applied by an elongated pusher 152 extending distally from a rear button 150 disposed in a proximal end of the housing 1100. The pusher 152 is dimensioned to be slidable within the space defined by the channel 334 and the top surfaces of the carriages 202, 204, and preferably has a width less than or equal to the width of the channel 334 and a height less than or equal to the first depth of the channel 334. As the distal end of the pusher 152 is pushed against the inclined face 276, a transverse force is applied to the post 272, causing the deflecting portion 260 to deflect transversely. The rear button 150 may be attached to an interior wall of the housing 1100 by a pair of flexible wings 156 to provide resiliency. In at least one embodiment, the flexible arms wings 156 are connected to arm rests 144. In other embodiments, the rear button 150 may include a biasing means, such as a helical spring, disposed between the rear button 150 and the interior of the housing 1100 to provide resiliency. In a preferred embodiment, the rear button 150 may be depressed approximately 3 mm into the housing 1100.

In the embodiment pictured in FIG. 11C, the pusher 152 is approximately as wide as the channel 334 in order to stabilize the pusher 152 as it is advanced longitudinally. The distal tip 154 of the pusher 152 may have a width less than a lateral width of the inclined face 276, in order to wedge between the inclined face 276 and a wall of the channel 334. In other embodiments, the distal tip 154 of the pusher 152 may be wider than the inclined face 276. In a further preferred embodiment, the width of the channel 334 is greater than or equal to the width of the distal tip 154 plus the width of the post 272, such that the distal tip 154 and post 272 may fit side-by-side within the channel 334 when the distal tip 154 is in contact with the catch 336.

In the embodiment pictured in FIG. 11C, the distal tip 154 terminates in flat face normal to the longitudinal axis. However, the distal tip 154 and inclined face 276 may be configured in a variety of shapes to produce a transverse force on the deflecting portion 260. In some embodiments, the inclined face 276 may be normal to the longitudinal axis, while the distal tip 154 is provided with a sharply angled tip. In other embodiments, the inclined face 276 or the distal tip 154 or both may be provided with curved surfaces.

Because the catcher 330 is used to retain the carriage assembly 200 in an armed state, the catcher 330 must remain proximally retracted until firing. In one embodiment shown in FIGS. 15, 16, and 16A, the device is provided with a lockout assembly 500 in order to prevent the lever 1310 from being operated and inadvertently advancing the catcher 330 when the device is in an armed state. The lockout assembly 500 comprises a blocker 510, a lever release 520 and a second biasing element 530.

The lever release 520 comprises a slidable switch 522 disposed in a side of the housing 1100 and a latch 524 to engage the lever 1310. In the embodiment shown in FIG. 16A, the latch 524 is a proximally facing protrusion that engages a ledge 314 on the underside of the lever 1310. The latch 524 may be released by sliding the lever release 520 distally off of the ledge 314. The lever release 520 is biased proximally by the second biasing element 530 to keep the latch 524 engaged with the lever 1310 when the lever release 520 is not being operated.

The lever release 520 may optionally be provided with an inclined surface 526, which engages an abutment 316 on the underside of the lever 1310. When the lever release 520 is advanced distally, the inclined surface 526 contacts the abutment 316 and drives the lever 1310 upward away from the device. It is believed that the separating action of the lever release 520 enables a user to more easily grasp the lever 1310. In some embodiments, the slidable switch 522 may be a generally rectangular extrusion having a flat face, although other shapes are within the scope of invention. In other embodiments, the slidable switch 522 may include a raised portion 528 on one side and the face may be sloping or curved. It is believed that the raised portion 528 facilitates movement of the slidable switch 522 using the thumb or a single finger.

Figure 15:
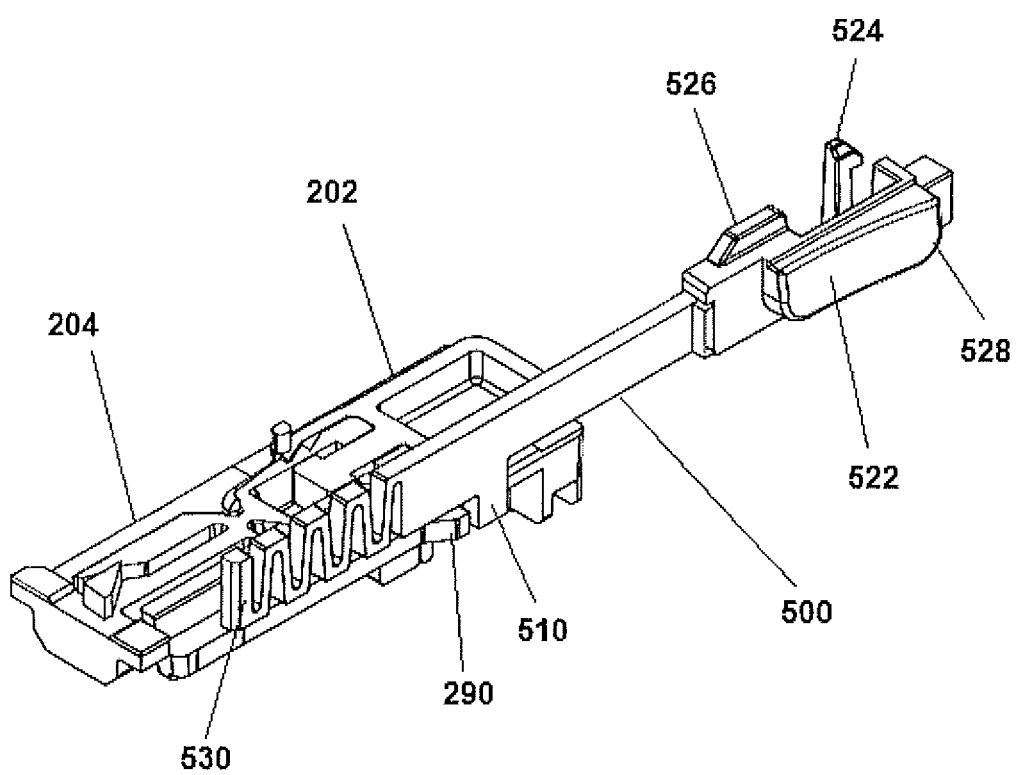
FIG. 15 is a perspective view of the carriage assembly and lockout assembly according to one embodiment of the prior art.

The blocker 510 may be a protuberance extending downwardly to engage a side tab 290 extending from the front carriage 204, as illustrated in FIG. 15. When the device is not armed, the front carriage 204 is positioned near a distal end of the housing 1100. In that position, the side tab 290 is located distally of and separated from the blocker 510. Because the blocker 510 and side tab 290 are separated, the lever release 520 may be operated, compressing the second biasing element 530 and advancing the blocker 510 distally. After the device is armed, the front carriage 204 is retracted proximally, and the side tab 290 abuts the blocker 510. In that position, the blocker 510 is prevented from advancing distally by the side tab 290. Consequently, the second biasing element 530 cannot be compressed and the lever release 520 cannot be advanced. Because the lever release 520 remains biased proximally, the latch 524 cannot be disengaged from the ledge 314, and the lever 1310 cannot be operated.

In other embodiments, a side tab 292 may extend from the rear carriage 202, and the side tab 292 of the rear carriage abuts the blocker 510 in the same manner as above. In embodiments comprising only a singular carriage, a side tab 294 may extend from the single carriage, and the side tab 294 of the singular carriage abuts the blocker 510 in the same manner as above.

Figure 16:
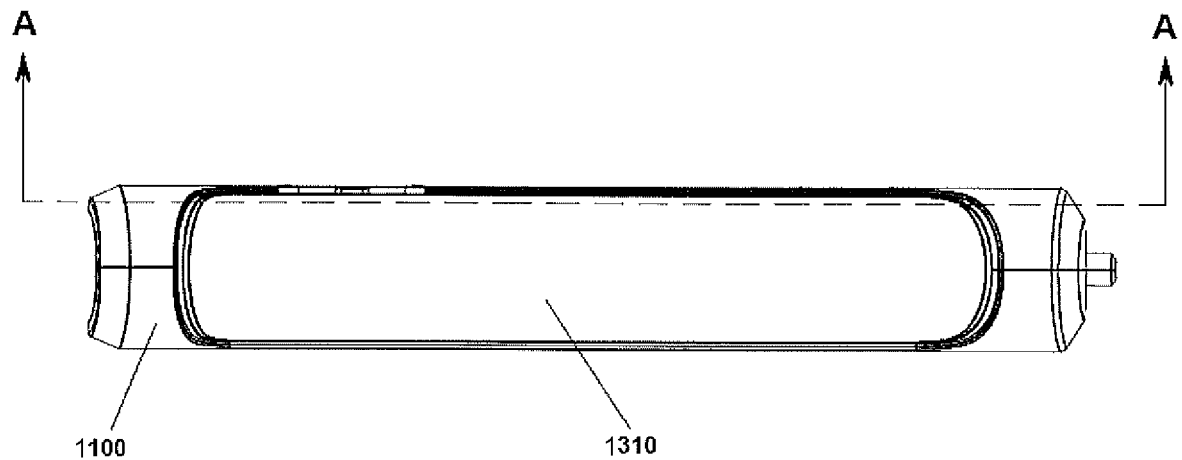
FIG. 16 is a top view of the lever, lockout assembly, and housing according to one embodiment of the prior art.
Figure 16A:
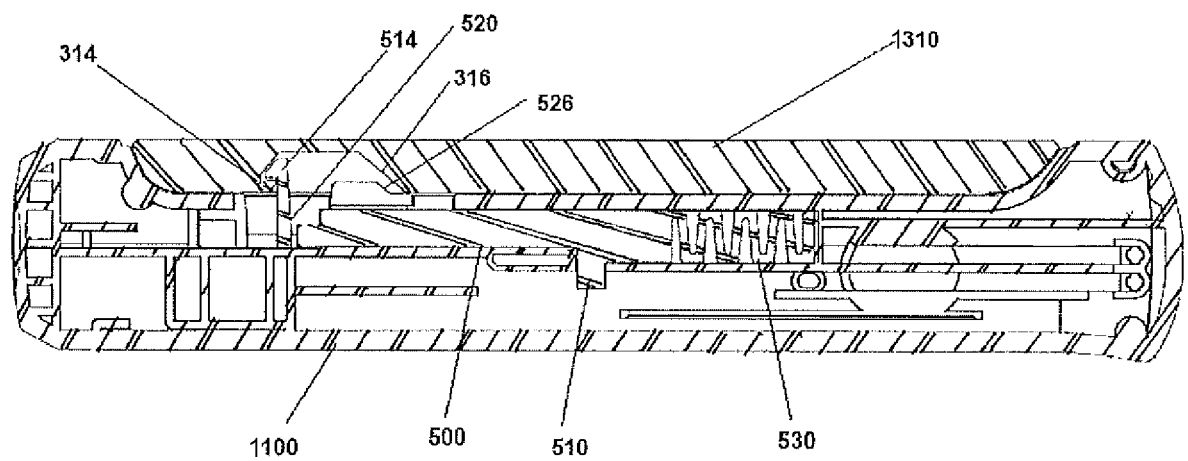
FIG. 16A is a cross-sectional view along lines A-A in FIG. 16.

In the embodiment depicted in FIGS. 15-16, the second biasing element 530 is integral with the lockout assembly 500 and is generally sinusoidal in shape. In other embodiments, the second biasing element 530 may be separately formed and may be any compressible element, including a helical spring. In further embodiments, the lever release 520 may be integral with the lockout assembly 500.

In at least one embodiment, the device is provided with a safety mechanism 700. As illustrated in FIGS. 10, 10A, 11, and 11A-C, the safety mechanism 700 comprises a safety switch 710 disposed in the side of the housing 1100 and an obstructer 720 extending into the housing 1100. The safety mechanism 700 is slidable between a locked state and an unlocked state. In the locked state, the obstructer 720 is positioned between the deflecting portion 260 and an interior wall of the housing 1100, preventing the deflecting portion 260 from being deflected toward the interior wall. When the safety mechanism 700 is moved to the unlocked state, the obstructer 720 is moved out of position between the interior wall and the deflecting portion 260, and the deflecting portion 260 is free to deflect toward the interior wall.

When the safety mechanism 700 is in the locked state, the obstructer 720 preferably extends from the interior wall and contacts a face of the deflecting portion 260 in its neutral position. In other embodiments, however, the obstructer 720 may be shorter to allow a small degree of deflection where the catch 336 of the catcher 330 and the post 272 of the front carriage 204 are still substantially aligned.

In some embodiments, the safety 700 may include a flexible spring arm. The spring arm extends longitudinally and includes a bump 742 to engage one of a pair of detents 180 on an interior wall of the housing 1100. In a neutral position, the projection is engaged into one of the two detents. As sufficient longitudinal force is applied to the safety 700, the bump 742 is pushed out of the detent 180 and the spring arm flexes slightly against the housing 1100. When the spring arm reaches the other detent 180, the bump 742 engages the detent 180, and the spring arm returns to a neutral position.

In the embodiments shown in FIGS. 10, 10A, 11, and 11A-C, the safety switch 710 is oriented longitudinally and positioned near the distal end of the housing 1100. In other embodiments, however, the safety switch 710 may be rotated with respect to the lateral axis or repositioned on the housing 1100 so that the obstructer 720 prevents flexing of the deflecting portion 260 in the locked state. In further embodiments, the safety switch 710 may be an elliptical extrusion having a flat face, although other shapes are within the scope of invention. In still further embodiments, the safety switch 710 may include a crest 712 transverse to the direction of movement and having sloping or concave sides. It is believed that the crest 712 facilitates movement of the safety switch 710 using the thumb or a single finger.

The housing 1100 may be further provided with an indicator window 160, as shown in FIG. 1, through which a portion of the rear or front carriage 202, 204 is visible when the device is in an armed state and not visible through the window 160 when the device is in any other state. Preferably, the visible portion of the carriage 202, 204 is provided with a marking, such as a contrasting coloration, a painted symbol, or etching.

As it can be appreciated, the pincer 942 of the prior art outer cannula 940 must insert into the window 932 perfectly in order for the pincer 942 to sever the core from the target tissue 14. Any small defect in the shape or angle of the pincer 942 or any deviation in its movement may cause the pincer 942 to strike the outer surface of the inner cannula 930 rather than entering the window 932. Failure of the pincer 942 to insert properly will result in a failure to collect the sample and may also permanently damage the device 900. The present invention seeks to improve upon the prior art by using a core-severing cannula 120 in place of the pincer 942 and window 932.

FIG. 19 shows one embodiment of the present invention. The needle set 100 comprises a stylet 130, a core-cutting cannula 110 and a core-severing cannula 120. Preferably, the stylet 130 is a solid trocar ground stylet having a three-sided point 132 although other configurations of stylets are within the scope of the invention. The stylet 130 is positioned coaxially inside the core-cutting cannula 110 and is slidable within the core-cutting cannula 110.

The core-cutting cannula 110 is a hollow tube having at its distal end at least one cutting edge 112. In the embodiment shown in FIG. 19, the core-cutting cannula 110 includes three arcuate and beveled cutting edges 112 formed between three points 114. The points 114 are sharp and are configured to easily penetrate the tissue, while the beveled cutting edges 112 separate the core from the surrounding tissue 14 through a knifing action. The core-cutting cannula 110 is positioned coaxially inside the core-severing cannula 120 and is slidable within the core-severing cannula 120.

The core-severing cannula 120 is a hollow tube having at its distal end a plurality of fingers 122. The fingers 122 are preferably formed integrally with the tubular portion of the core-severing cannula 120 by laser cutting. However, in other embodiments, the fingers may be formed as separate elements and subsequently attached to the distal end of the tubular portion of the core-severing cannula 120 by any conventional means such as welding.

Figure 27A:
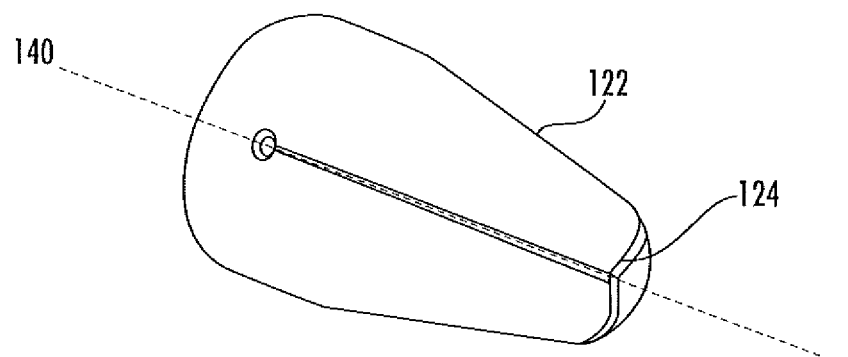
FIG. 27A is a perspective view of the fingers of the core-severing cannula of FIG. 26A, showing the fingers in the closed position.
Figure 27B:
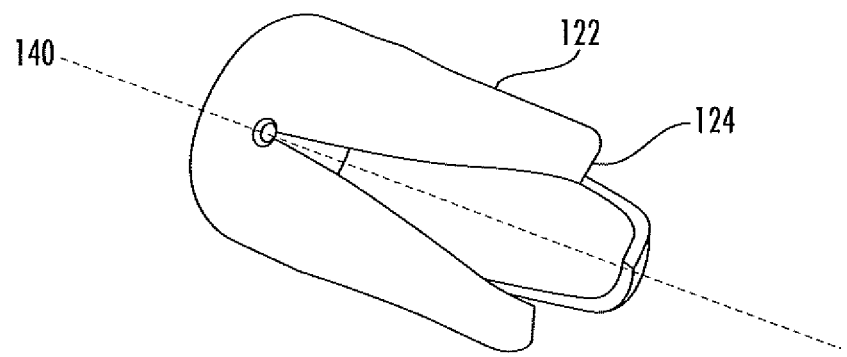
FIG. 27B is a perspective view of the fingers of the core-severing cannula of FIG. 26A, showing the fingers in an intermediate position between the open and closed positions.
Figure 27C:
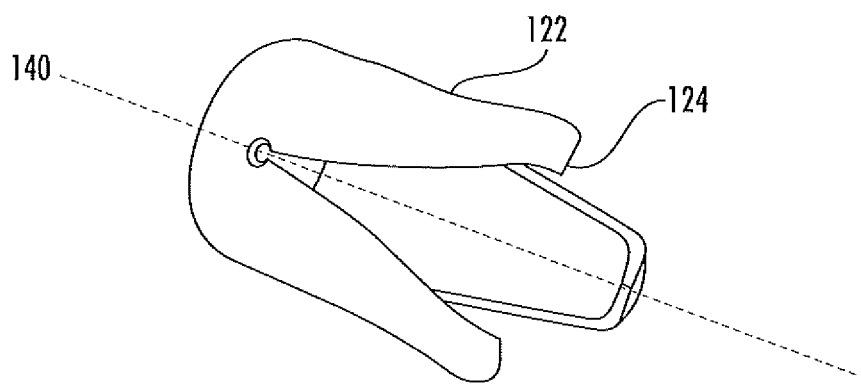
FIG. 27C is a perspective view of the fingers of the core-severing cannula of FIG. 26A, showing the fingers in the open position.

The fingers are capable of flexing between a closed position and an open position. FIGS. 27A-27C illustrate the sequence of opening. FIG. 27A shows the fingers in the closed position. In the closed position, the fingers are in a relaxed, unflexed state and generally resemble the shape of a truncated cone. The side edges 126 of each of the fingers are substantially parallel to those of the adjacent fingers. FIG. 27B shows the fingers in an intermediate position between the open and closed positions. As it can be seen, the distal ends of the fingers flex away from the center in directions substantially orthogonal to the longitudinal axis 140, resembling a blooming flower. FIG. 27C shows the fingers in the open position. In the open position, the fingers 122 are flexed apart sufficiently wide to allow passage of the core-cutting cannula 110, as depicted in FIG. 19A.

Preferably, the fingers 122 are formed from hyperelastic material such as Nitinol. However, other biologically compatible elastic materials are within the scope of the invention. The fingers are in a resting or unflexed state in the closed position, and are in a compressed or flexed state in the open position.

A typical procedure for using the device is shown in FIGS. 20-25 and includes the following steps:

First, the user inserts a coaxial introducer needle 400 into the target site 14. The coaxial introducer needle 400 comprises a hollow needle 410 and an introducer stylet 420 slidably disposed therein. The hollow needle 410 includes a hub 412 at its proximal end. Preferably, the hub 412 includes a connecting means 414 for connecting with other medical devices, such a luer connection. In the embodiment shown in FIG. 20, the introducer stylet 420 also includes a connector 424 at its proximal end, which is configured to mate with the connecting means 414 in order to keep the components of the coaxial introducer needle 400 together during insertion. The introducer stylet 420 terminates at its distal end in a sharp tip 422.

In the example shown in FIG. 20, the target site 14 is a lesion within surrounding healthy tissue 16. As the device is inserted, the sharp tip 422 of the introducer stylet 420 punctures the epidermis 12 and the healthy tissue 16 until the target site 14 is reached. Once the sharp tip 422 is properly located within the target site 14, the introducer stylet 420 is detached from the hollow needle 410 and is removed, while the distal end of the hollow needle 410 remains located in the target site 14 as shown in FIG. 21.

Next, the needle set 100 is attached to an appropriate biopsy device handle 300. At this stage, the proximal ends of the stylet 130, core-cutting cannula 110, and core-severing cannula 120 are connected to the internal mechanism (not shown) of a biopsy device handle 300. Prior to arming the device, the distal end of the core-severing cannula 120 is distal to the distal end of the core-cutting cannula 110, and the distal end of the core-cutting cannula 110 is distal to the distal end of the stylet 130. At this stage, the fingers 122 of the core-severing cannula 120 are in the closed position.

Preferably, the needle set 100 is used with a biopsy device having a two-stage carriage element, similar to the two stage-carriage element as described above, and is connected to the biopsy device handle 300 in the same manner as in prior art biopsy needles. More specifically, the proximal end of the stylet 130 is fixed relative to the housing of the biopsy device handle 310, the proximal end of the core-cutting cannula 110 is attached to the front portion of a two-stage carriage element, and the proximal end of the core-severing cannula 120 is attached to the rear portion of a two-stage carriage element. However, it can be appreciated that the needle set 100 of the present invention may be used with other biopsy device handles. Suitable biopsy handles will include mechanisms that provide a first means for extending an inner cannula 930 a short distance in a distal direction and a second means for extending an outer cannula 940 a slightly longer distance in a distal direction.

Once the needle set 100 is connected to the biopsy device handle 300, the biopsy device is armed for activation. In the embodiment shown in FIG. 22, the device is cocked by opening and closing the lever 312 on the handle portion 310. That action retracts the front and rear carriage portions against a biasing element, simultaneously revealing the distal end of the stylet 130.

With reference to the sequence shown in FIGS. 27A-C, as the cannulas 110, 120 are retracted, the fingers 122 of the core-severing cannula 120 are forced apart by the three-sided point 132 of the stylet 130, with the facets of the stylet 130 acting as ramps to guide the opening motion. The core-severing cannula 120 is further retracted relative to the core-cutting cannula 110, causing the fingers to assume the open position, at which point the fingertips 124 rest on the outside surface of the core-cutting cannula 110 as shown in FIG. 19A. The fingers 122 are radially spaced from the outside surface of the core-cutting cannula 110. The needle set 100 of the armed biopsy device 300 is then inserted into the hollow needle 410 and the distal end of the stylet 130 is advanced to the target site 14.

Figure 23:
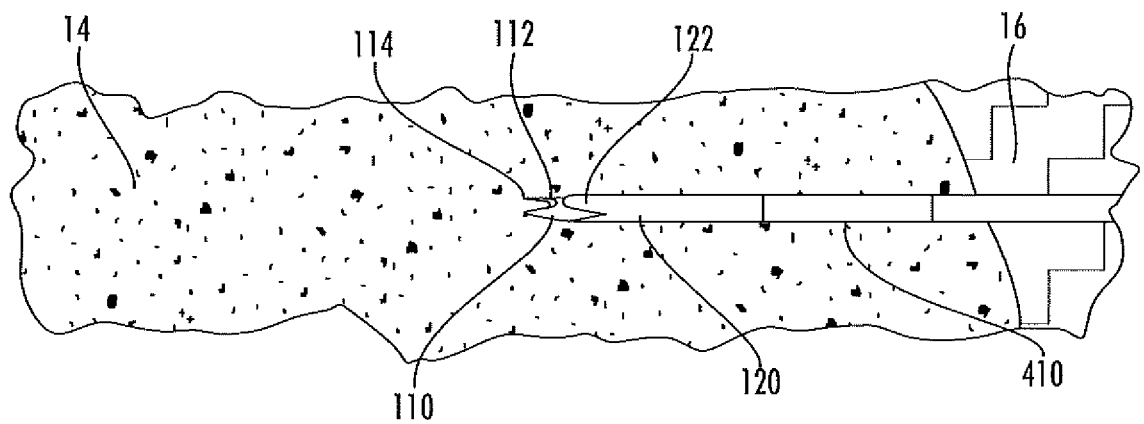
FIG. 23 is a side plan view of the needle set in accordance with the invention, showing placement in the target tissue after the biopsy device has been armed.

FIG. 23 shows the needle set 100 when the biopsy device is in an armed state. At this stage, the distal end of the stylet 130 is positioned proximally of the distal ends of the core-cutting cannula 110 and core-severing cannula 120, and the distal end of the core-cutting cannula 110 is positioned distally of the distal end of the core-severing cannula 120.

Figure 24:
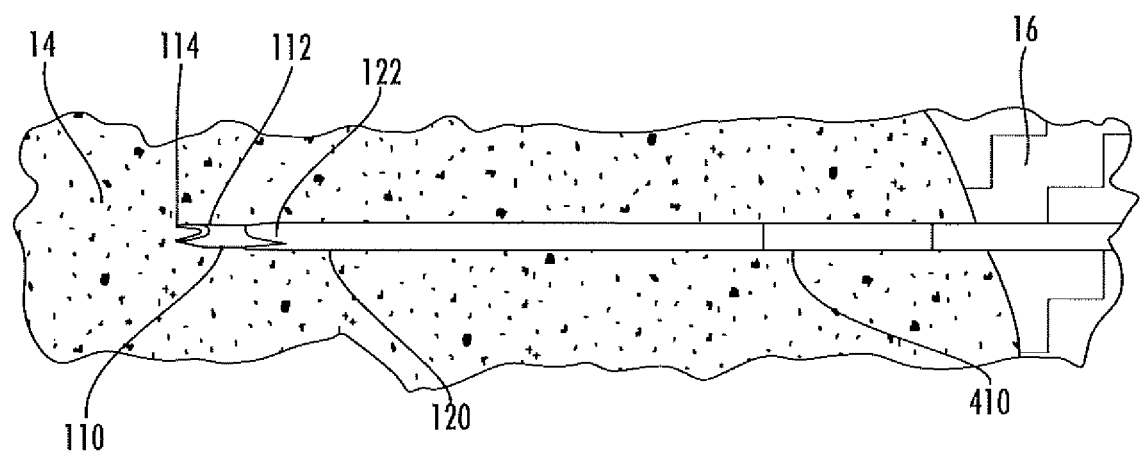
FIG. 24 is a side plan view of the needle set of FIG. 23, showing positioning of the needle set immediately after the core has been cut from the surrounding tissue.

The user then activates the device to begin the firing sequence. Activation of the device causes the front and rear carriage portions to be released from a catch (not shown), causing the biasing element to force the carriages, a fixed distance in the distal direction. Since the proximal ends of the core-cutting cannula 110 and core-severing cannula 120 are connected, respectively, to the front and rear carriages, the core-cutting cannula 110 and core-severing cannula 120 are also forced distally relative to the stylet 130, as shown in FIG. 24. As the points 114 of the core-cutting cannula 110 extend beyond the stylet 130, the sharp points 114 penetrate the tissue of the target site 14. As the core-cutting cannula 110 continues to extend, the cutting edges 112 sever a generally cylindrical core 18 of tissue away from the surrounding tissue of the target site 14.

Figure 25:
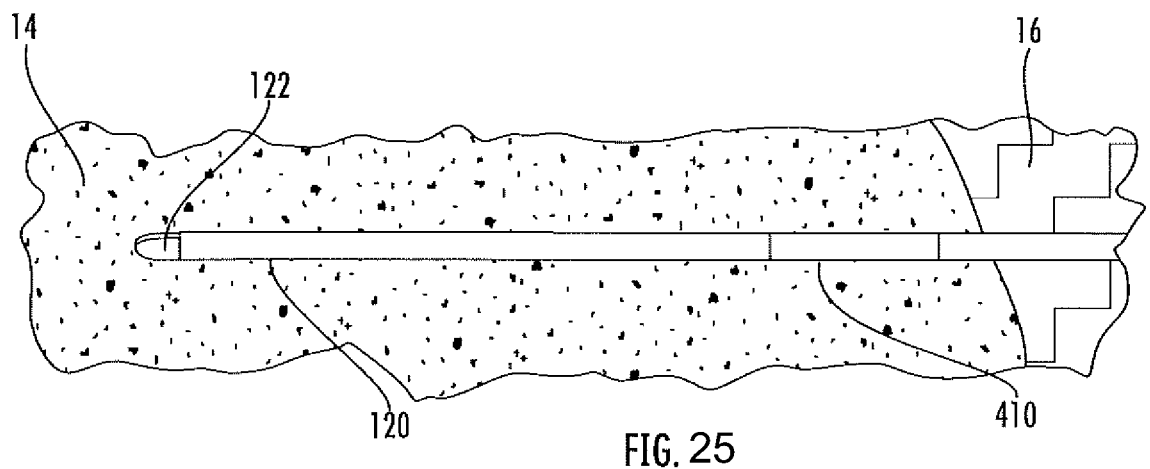
FIG. 25 is a side plan view of the needle set of FIG. 24, showing positioning of the needle set immediately after the core has been severed.
Figure 26A:
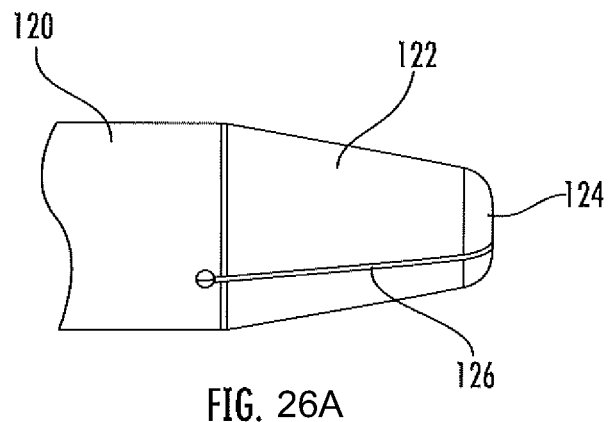
FIG. 26A is a partial side plan view of the distal end of a core-severing cannula according to the invention.
Figure 26B:
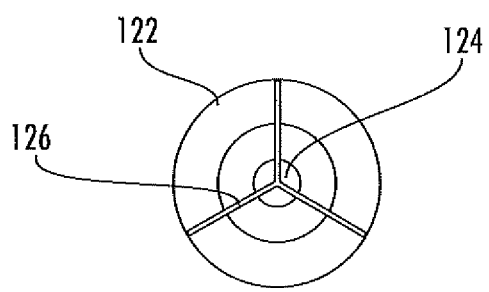
FIG. 26B is a front plan view of the core-severing cannula of FIG. 26A.
Figure 26C:
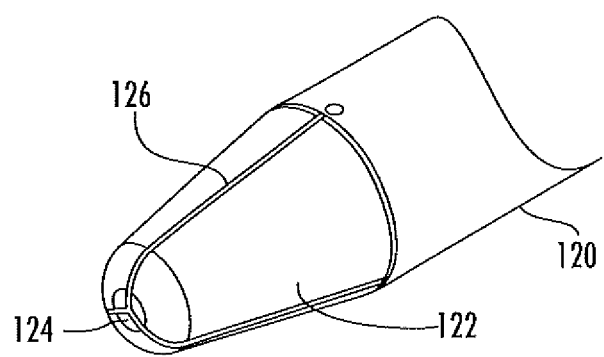
FIG. 26C is a partial perspective view of the core-severing cannula of FIG. 26A.

At a predetermined depth, the distal motion of the front portion of the carriage is arrested, and the core-cutting cannula 110 reaches its maximum penetration depth. However, due to the two-stage carriage mechanism, the rear carriage continues to move distally a short distance relative to the front carriage. As the core-severing cannula 120 continues to move distally relative to the core-cutting cannula 110, the fingertips 124 slide distally beyond the points 114 of the core-cutting cannula 110. Since the fingertips 124 are no longer forced open by the core-cutting cannula 110, they begin to flex together and assume the closed position, as shown in FIG. 25. As the fingers close, the fingertips 124 squeeze the core along a plane normal to its longitudinal axis. The squeezing force shears the core and separates it from the surrounding tissue 14. Since the fingers 122 are in the closed position, the severed core is retained within the core-cutting cannula 110.

After the firing sequence has completed, the device is removed from the hollow needle 410. The severed core may then be ejected from core-cutting cannula 110. In the embodiment shown in FIG. 19, removal of the core may be accomplished by arming the device again. As described above, the arming action causes the fingers 122 of the core-severing cannula 120 to be forced apart into the open position, at which point the severed core may exit the core-cutting cannula 110 through its distal opening.

Another embodiment of the core-severing needle according to the invention is shown in FIGS. 28A-28C and 29A-29D. This embodiment is similar to the embodiment of FIGS. 10A-26C and 27A-27C, and comprises a core cutting cannula 110 having a plurality of sharp points 114 at its distal end and arcuate cutting edges 112 between the points, a stylet 130 having a sharp tip 132, and a core-severing cannula 220 comprising three fingers 222. However, the second embodiment differs from the first embodiment in that the fingertips 224 are not formed along straight lines.

Figure 28A:
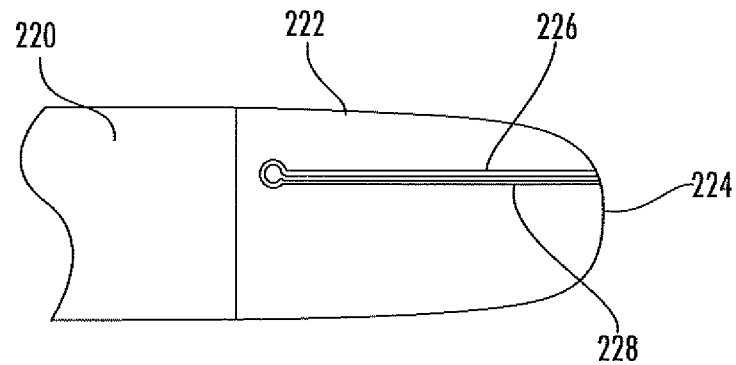
FIG. 28A is a partial side plan view of the distal end of a core-severing cannula according to a second embodiment of the invention.
Figure 28B:
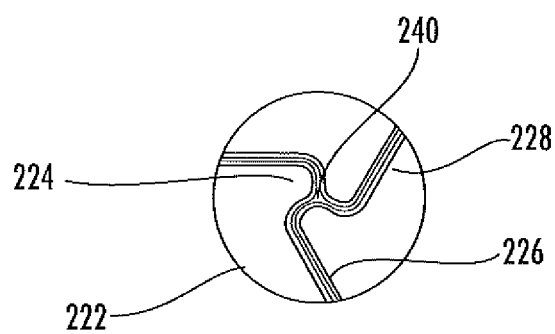
FIG. 28B is a front plan view of the core-severing cannula of FIG. 28A.
Figure 28C:
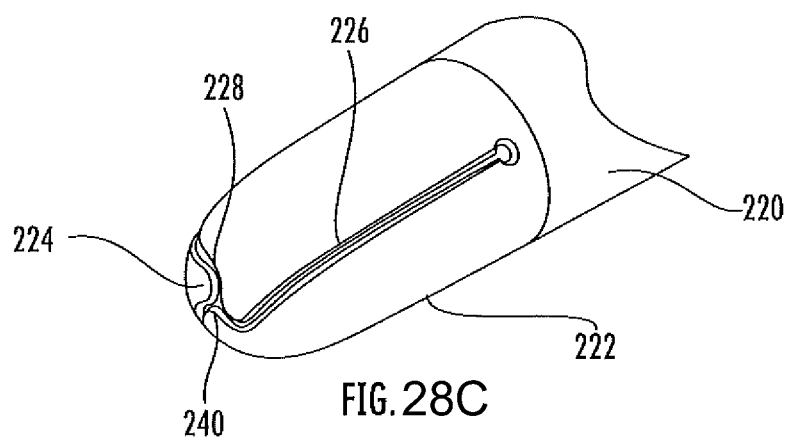
FIG. 28C is partial perspective view of the core severing cannula of FIG. 28A.

As seen in FIG. 28A-28C, a first edge 226 of the fingertip 222 extends in a substantially straight line that is off-center. A second edge 228 of the fingertip 222 extends initially toward the first edge 226, then curves in an arc toward the center 240 of the three fingers 222. The first 226 and second 228 edges then come together in an arcuate shape to form an asymmetric fingertip 222. When viewed head-on in a distal-to-proximal direction, the fingers 222 superficially resemble a camera's diaphragm shutter. However, unlike a camera diaphragm, the three fingers 222 do not rotate relative to the center 240. Instead, as with the embodiment shown in FIGS. 27A-11D, the fingertips 224 flex apart in directions substantially normal to a longitudinal axis.

Figure 29A:
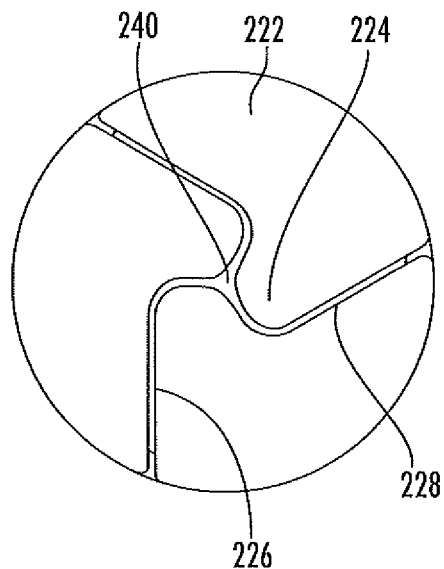
FIG. 29A is front plan view of the fingers of the core severing cannula of FIG. 28A, showing the fingers in the closed position.
Figure 29C:
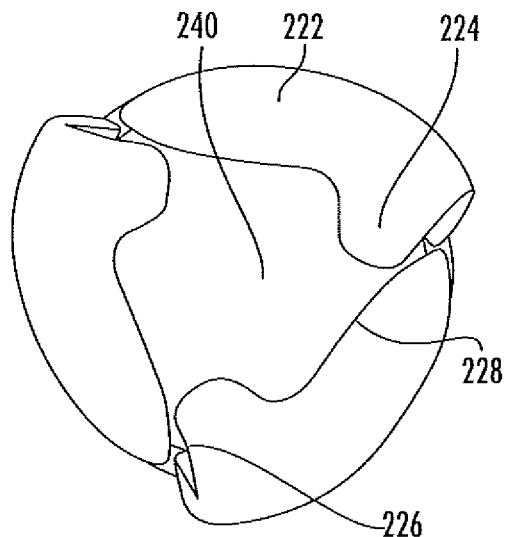
FIG. 29C is a front plan view of the fingers of the core-severing cannula of FIG. 28A, showing the fingers in a more opened position than in FIG. 29B.
Figure 29B:
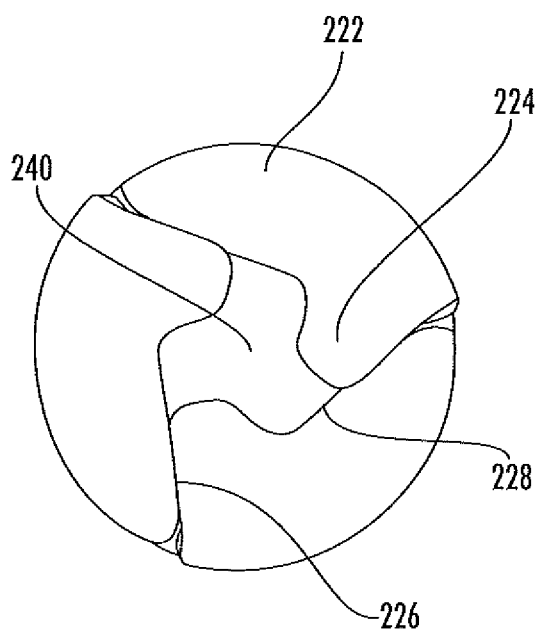
FIG. 29B is a front plan view of the fingers of the core-severing cannula of FIG. 28A, showing the fingers in a partially opened position.
Figure 29D:
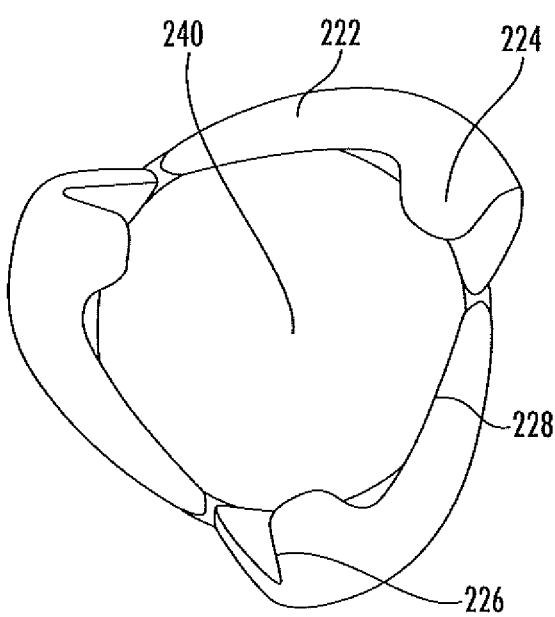
FIG. 29D is a front plan view of the fingers of the core-severing cannula of FIG. 28A, showing the fingers in the open position.

FIGS. 29A-29D show the sequence of opening. In FIG. 29A, the fingers 222 are in a closed position. The first edge 226 of one finger is substantially parallel to the second edge 228 of an adjacent finger 222. FIGS. 29B and 29C show the fingers 222 in intermediate stages between the open and closed positions. FIG. 29D shows the fingers 222 in the open position. In the open position, the fingers 222 are flexed apart sufficiently wide to allow passage of the core-cutting cannula 110.

It is believed that the fingers 222 shaped according to the embodiment shown in FIGS. 28A-28C and 29A-29D are beneficial because they provide two modes of cutting during closing. Specifically, due to the asymmetrical design, the edges 226, 228 of the fingers 222 slide relative to one another in axial and radial directions as the fingers 222 close. This motion causes the edges 226, 228 of the fingers to simultaneously apply both squeezing and shearing forces to the base of the core, which may result in more complete separation from the target site 14.

Internal testing has shown promising results. In particular, the novel core-severing cannula of the present invention has been shown to result more frequently in the collection of more complete samples compared to prior art cannulas.

Although the present invention has been described in relation to particular embodiments thereof, it can be appreciated that other variations and modifications will be apparent to those skilled in the art without departing from the teaching of the invention. Therefore, the present invention is not limited by the specific disclosure herein, but only by the claims.

We claim:

1. A core-severing biopsy needle set comprising an inner cannula having at its distal end at least one cutting edge and an outer cannula slidably disposed around and coaxially to the inner cannula, the outer cannula having at its distal end a plurality of flexible fingers having first and second side edges that intersect at a distal end to form a fingertip which is asymmetrical with respect to a radial axis of the outer cannula, the flexible fingers capable of moving between a closed position and an open position when the inner cannula is inserted through the flexible fingers, wherein in the closed position the first side edges of each flexible finger is substantially parallel to the second side edge of an adjacent flexible finger, and wherein in the open position the fingertips are positioned outside the exterior surface of the inner cannula, wherein the first and second side edges of the flexible fingers are asymmetrical with respect to a longitudinal axis of the outer cannula, and the flexible fingers are capable of moving between the closed position and the open position such that the first and second side edges of the flexible fingers slide relative to one another in axial and radial direction as the flexible fingers close upon retraction of the inner cannula from the flexible fingers.

2. The core-severing biopsy needle set of claim 1, further comprising a stylet slidably disposed within and coaxial to the inner cannula.

3. The core-severing biopsy needle set of claim 2, wherein the stylet terminates at its distal end in a sharp three-faceted point.

4. The core-severing biopsy needle set of claim 1, wherein the distal end of the inner cannula includes a plurality of sharp points and an equal number of cutting edges, the cutting edges being arcuately shaped and positioned between sharp points.

5. The core-severing biopsy needle set of claim 4, wherein the cutting edges are formed by beveling the distal edge of the inner cannula.

6. The core-severing biopsy needle set of claim 1, wherein the outer cannula includes three fingers.

7. The core-severing biopsy needle set of claim 1, wherein the fingers in the closed position form a substantially conical shape, tapering from the proximal end to the distal end.

8. The core-severing biopsy needle set of claim 1, wherein the fingers are formed integrally with the outer cannula.

9. The core-severing biopsy needle set of claim 1, wherein the outer cannula is formed by laser cutting.

10. The core-severing biopsy needle set of claim 1, wherein the outer cannula is formed from hyperelastic material.

11. The core-severing biopsy needle set of claim 1, wherein in the closed position, the fingertips are positioned distally of the distal end of the inner cannula.

12. A biopsy device comprising:
a handle portion defining a longitudinal axis;
an inner cannula having at its distal end at least one cutting edge;
an outer cannula slidably disposed around and coaxially to the inner cannula and having at its distal end a plurality of flexible fingers having first and second side edges that intersect at a distal end to form a fingertip which is asymmetrical with respect to a radial axis of the outer cannula, the flexible fingers capable of moving between a closed position and an open position when the inner cannula is inserted through the flexible fingers, wherein in the closed position the first side edges of each flexible finger is substantially parallel to the second side edge of an adjacent flexible finger, and wherein in the open position the fingertips are positioned outside the exterior surface of the inner cannula, wherein the first and second side edges of the flexible fingers are asymmetrical with respect to a longitudinal axis of the outer cannula, and the flexible fingers are capable of moving between the closed position and the open position such that the first and second side edges of the flexible fingers slide relative to one another in axial and radial direction as the flexible fingers close upon retraction of the inner cannula from the flexible fingers;
wherein the handle portion further comprises a two-stage carriage element, the two-stage carriage element having a flexible abutment, the inner cannula being connected at a proximal end to a first stage of the two-stage carriage element, and the outer cannula being connected at a proximal end to a second stage of the two-stage carriage element;
a catch overlapping at least a portion of the abutment in a longitudinal direction;
a first trigger disposed in the housing and movable longitudinally within the housing and contacting a portion of the flexible abutment wherein longitudinal movement of the first trigger causes a first contact force to be applied to the abutment;
a second trigger disposed in the housing and movable transversely within the housing and contacting a portion of the flexible abutment wherein transverse movement of the second trigger causes a second contact force to be applied to the abutment; and wherein the abutment is configured to flex away from the catch when forced by either the first or second contact force, such that the catch does not overlap a portion of the abutment and the first and second stages are biased distally together to a predetermined distance whereupon movement of the first stage is arrested, and wherein after the first stage is arrested, the second stage is further biased distally to a predetermined depth whereupon movement of the second stage is arrested.

13. The biopsy device of claim 12, wherein after arrest of the first stage, the flexible fingers are in the open position, and wherein after arrest of the second stage, the flexible fingers are in the closed position.

14. The biopsy device of claim 12, further comprising a stylet slidably disposed within the inner cannula wherein prior to the first or second trigger contacting the flexible abutment, a distal end of the stylet extends distally beyond the distal end of the at least one cutting edge, and wherein after the first or second trigger contacting the flexible abutment, the distal end of the stylet is positioned proximally of the at least one cutting edge.

15. The biopsy device of claim 12, wherein prior to the first or second trigger contacting the flexible abutment, the flexible fingers are in the closed position, and wherein after the first or second trigger contacts the flexible abutment the flexible fingers are in the open position.

\* \* \* \* \*